(12) United States Patent
Machida et al.

(10) Patent No.: US 10,092,264 B2
(45) Date of Patent: Oct. 9, 2018

(54) IMAGE PROCESSING APPARATUS, IMAGE PROCESSING METHOD, RADIATION IMAGING SYSTEM, AND NON-TRANSITORY COMPUTER-READABLE STORAGE MEDIUM

(71) Applicant: CANON KABUSHIKI KAISHA, Tokyo (JP)

(72) Inventors: Yoshihito Machida, Sagamihara (JP); Tetsuo Shimada, Hachioji (JP); Osamu Tsujii, Kawasaki (JP); Akira Yoshino, Tokyo (JP); Maiko Sato, Yokohama (JP); Hidehiko Morinaga, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 55 days.

(21) Appl. No.: 15/228,240

(22) Filed: Aug. 4, 2016

(65) Prior Publication Data

US 2017/0055929 A1    Mar. 2, 2017

(30) Foreign Application Priority Data

Aug. 27, 2015 (JP) ................... 2015-168086
Aug. 28, 2015 (JP) ................... 2015-169728

(51) Int. Cl.
| | |
|---|---|
| *G06K 9/00* | (2006.01) |
| *A61B 6/00* | (2006.01) |
| *G06T 7/00* | (2017.01) |
| *G06T 7/33* | (2017.01) |
| *A61B 6/02* | (2006.01) |

(52) U.S. Cl.
CPC ............ *A61B 6/5235* (2013.01); *A61B 6/466* (2013.01); *A61B 6/502* (2013.01); *A61B 6/54* (2013.01); *G06T 7/0014* (2013.01); *G06T 7/33* (2017.01); *A61B 6/025* (2013.01); *A61B 6/5205* (2013.01); *G06T 2200/04* (2013.01);
(Continued)

(58) Field of Classification Search
None
See application file for complete search history.

(56) References Cited

U.S. PATENT DOCUMENTS

| | | | | |
|---|---|---|---|---|
| 7,653,263 B2* | 1/2010 | Wheeler | ................. | G06T 7/001 |
| | | | | 382/294 |
| 8,401,267 B2* | 3/2013 | Nakai | .................... | A61B 6/032 |
| | | | | 382/132 |

(Continued)

FOREIGN PATENT DOCUMENTS

| | | |
|---|---|---|
| JP | 2011-041585 A | 3/2011 |
| JP | 2011-224355 A | 11/2011 |
| JP | 2013-085560 A | 5/2013 |

*Primary Examiner* — Soo Park
(74) *Attorney, Agent, or Firm* — Fitzpatrick, Cella, Harper & Scinto

(57) ABSTRACT

An image processing apparatus obtains a three-dimensional radiation image of a right region of substantially symmetrical regions, obtains a three-dimensional radiation image of a left region of the substantially symmetrical regions, performs alignment between the three-dimensional radiation image of the right region and the three-dimensional radiation image of the left region based on a feature position of the regions, and substantially symmetrically arranges and displays the three-dimensional radiation image of the right region and the three-dimensional radiation image of the left region which have been aligned.

12 Claims, 32 Drawing Sheets

(52) U.S. Cl.
CPC ............... *G06T 2207/10081* (2013.01); *G06T 2207/30068* (2013.01); *G06T 2207/30096* (2013.01)

(56) References Cited

U.S. PATENT DOCUMENTS

| | | | |
|---|---|---|---|
| 8,730,234 B2 | 5/2014 | Iizuka et al. | |
| 8,855,382 B2* | 10/2014 | Sugiura | G01R 33/5608 382/128 |
| 2007/0003117 A1* | 1/2007 | Wheeler | G06T 7/001 382/128 |
| 2007/0003118 A1* | 1/2007 | Wheeler | G06T 7/001 382/128 |
| 2007/0014448 A1* | 1/2007 | Wheeler | G06T 7/0012 382/128 |
| 2007/0161886 A1* | 7/2007 | Kuth | G06K 9/6206 600/407 |
| 2009/0016580 A1* | 1/2009 | Yamamichi | A61B 6/502 382/128 |
| 2010/0022881 A1* | 1/2010 | Fujita | A61B 8/0825 600/445 |
| 2010/0166267 A1* | 7/2010 | Zhang | A61B 6/463 382/128 |
| 2011/0044520 A1* | 2/2011 | Nakai | A61B 6/032 382/131 |
| 2011/0110576 A1* | 5/2011 | Kreeger | G16H 50/50 382/132 |
| 2012/0014578 A1* | 1/2012 | Karssemeijer | G06T 7/0012 382/131 |
| 2012/0157819 A1* | 6/2012 | Jerebko | A61B 6/502 600/407 |
| 2016/0179346 A1 | 6/2016 | Machida | |
| 2016/0189401 A1 | 6/2016 | Machida | |
| 2016/0210743 A1* | 7/2016 | Schmidt | A61B 5/4064 |

* cited by examiner

X-Y PLANE: AXIAL SECTION
X-Z PLANE: SAGITTAL SECTION
Y-Z PLANE: CORONAL SECTION

RIGHT BREAST CC IMAGE    LEFT BREAST CC IMAGE

RIGHT BREAST MLO IMAGE    LEFT BREAST MLO IMAGE

FIG. 17
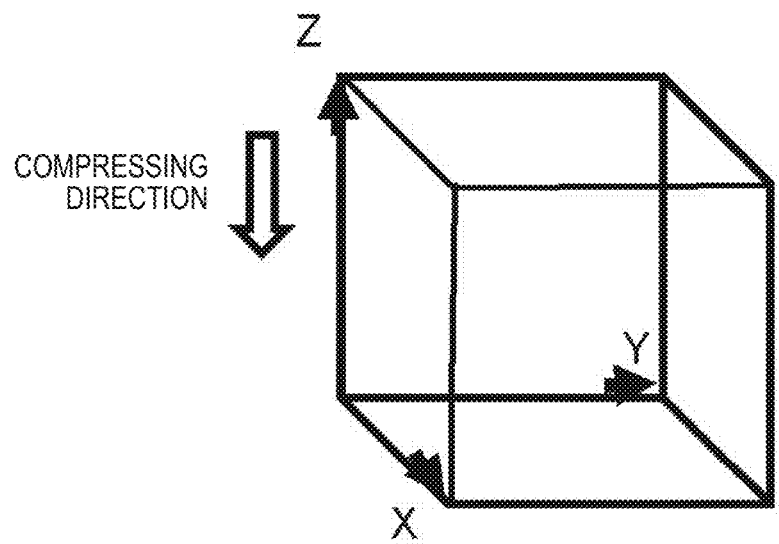
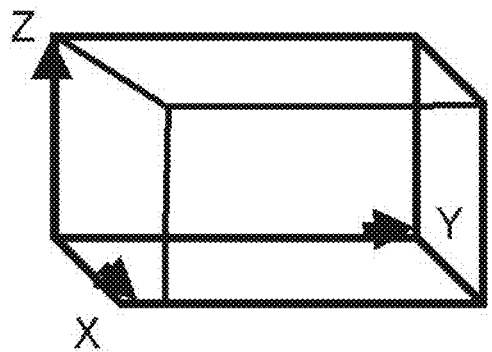

F I G. 25
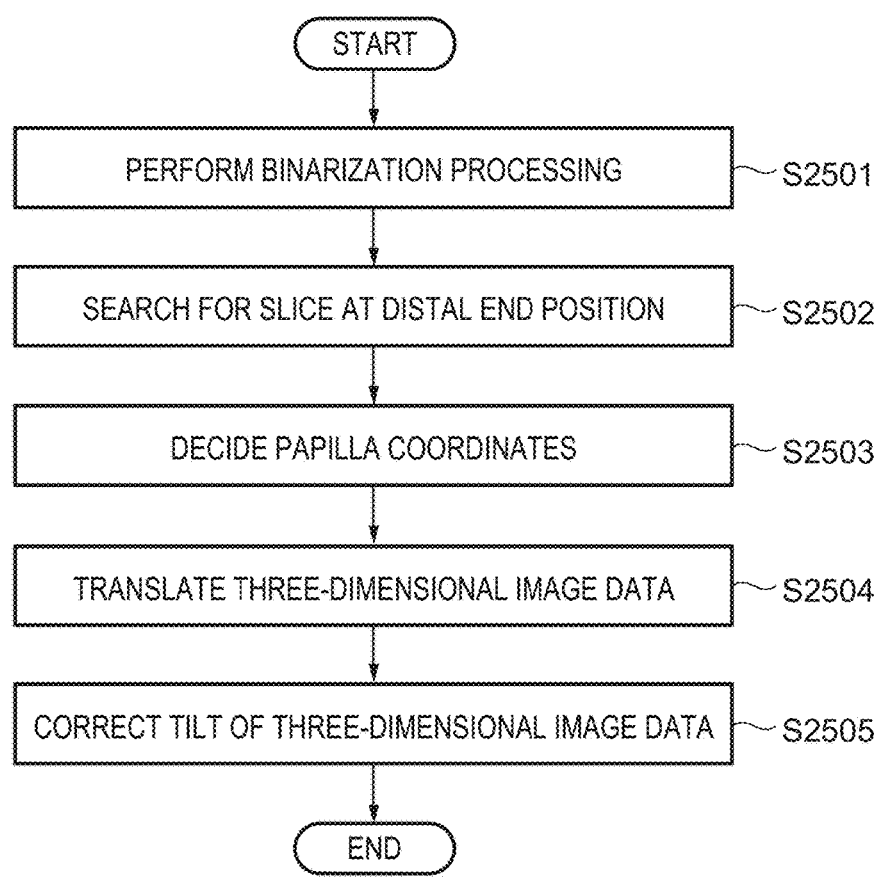

FIG. 26
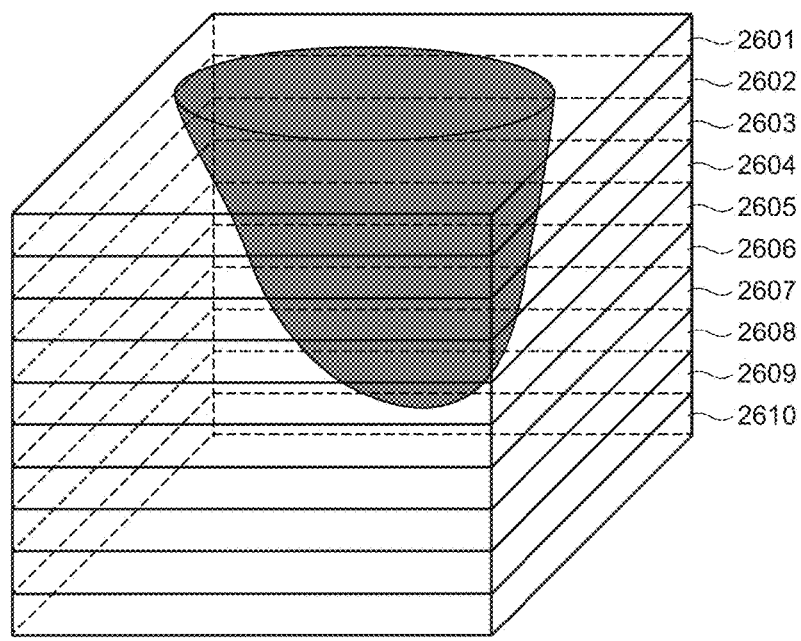
FIG. 27A    FIG. 27B
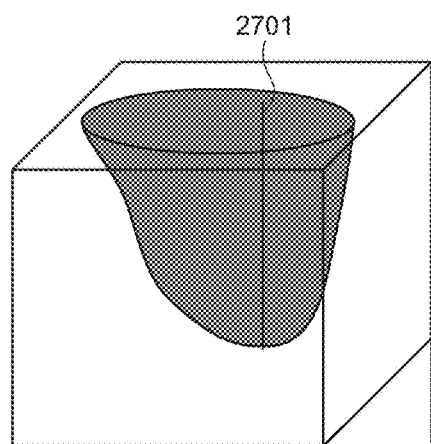
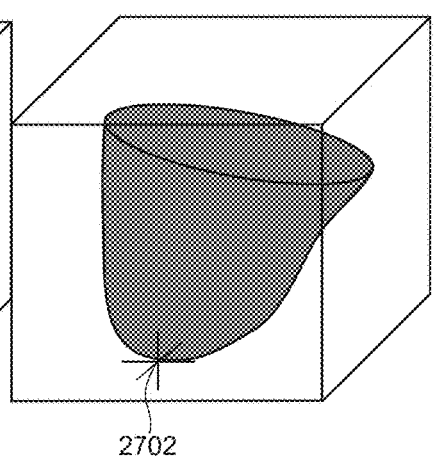

IMAGE PROCESSING APPARATUS, IMAGE PROCESSING METHOD, RADIATION IMAGING SYSTEM, AND NON-TRANSITORY COMPUTER-READABLE STORAGE MEDIUM

BACKGROUND OF THE INVENTION

Field of the Invention

The present invention relates to an image processing apparatus, an image processing method, a radiation imaging system, and a non-transitory computer-readable storage medium.

Description of the Related Art

As a radiation imaging system for examining breast cancer, a mammography apparatus is used. When, however, mammographing a dense breast (a breast with more mammary gland tissue), the lesion detection sensitivity and specificity may deteriorate because of the overlapping between a lesion portion and a mammary gland structure. As techniques of compensating for this drawback in mammography, tomosynthesis and breast-dedicated CBCT (Cone-Beam Computed Tomography) apparatuses have attracted much attention. These apparatuses are featured to provide 3D images of the breasts to allow observation of a lesion portion and a mammary gland structure in a separate state.

The related art includes the following technique. For example, pieces of predetermined tag information are extracted from a plurality of medical image data obtained by apparatuses available from different manufactures or of different models, and a grouping condition is set to recognize, as images of the same type, images each having one piece of tag information or a combination of a plurality of pieces of tag information of the extracted pieces of tag information.

There is proposed a medical image processing apparatus (see Japanese Patent Laid-Open No. 2011-41585), which determines a grouping condition with respect to images to be interpreted at the time of interpretation to recognize even images obtained by apparatuses available from different manufactures or with different model numbers as images of the same type as that of images used for layout setting, thereby enabling the reproduction of a layout.

Conventional medical image processing apparatuses have not been able to display radiation images of the right and left regions which are symmetrical to each other in association with each other. When separately imaging the right and left regions, in particular, the conventional medical image processing apparatuses have not been able to display the respective radiation images in association with each other.

SUMMARY OF THE INVENTION

According to one aspect of the present invention, there is provided an image processing apparatus which comprises: a right region image obtaining unit configured to obtain a three-dimensional radiation image of a right region of substantially symmetrical regions; a left region image obtaining unit configured to obtain a three-dimensional radiation image of a left region of the substantially symmetrical regions; an alignment unit configured to perform alignment between the three-dimensional radiation image of the right region and the three-dimensional radiation image of the left region based on a feature position of the regions; and a display control unit configured to substantially symmetrically arrange and display the three-dimensional radiation image of the right region and the three-dimensional radiation image of the left region which have been aligned.

Further features of the present invention will become apparent from the following description of exemplary embodiments (with reference to the attached drawings).

BRIEF DESCRIPTION OF THE DRAWINGS

FIG. 17 is a view showing how affine transformation is used as a compression model;

FIG. 25 is a flowchart showing alignment processing by the image processing apparatus 2104;

FIG. 26 is a schematic view showing three-dimensional image data of the breast;

FIGS. 27A and 27B are views showing an example of the adjustment of three-dimensional image data of the right and left breasts by the image processing apparatus 2104;

DESCRIPTION OF THE EMBODIMENTS

First Embodiment

Figure 1:
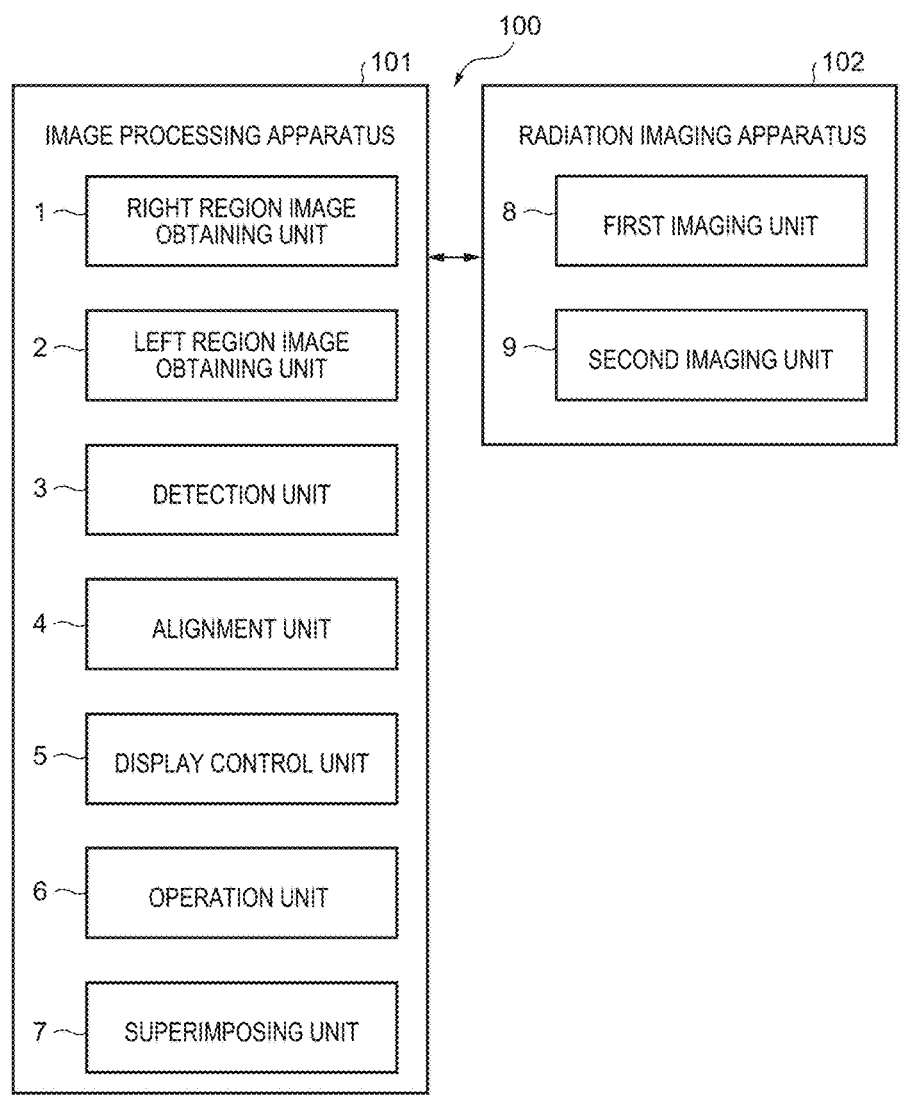
FIG. 1 is a block diagram showing an example of a radiation imaging system according to the first embodiment.

An example of an embodiment of the present invention will be described in detail with reference to the accompanying drawings. FIG. 1 is a block diagram showing an example of a radiation imaging system according to this embodiment. A radiation imaging system 100 includes an image processing apparatus 101 and a radiation imaging apparatus 102. The image processing apparatus 101 includes a right region image obtaining unit 1, a left region image obtaining unit 2, a detection unit 3, an alignment unit 4, a display control unit 5, an operation unit 6, and a superimposing unit 7. The radiation imaging apparatus 102 includes a first imaging unit 8 and a second imaging unit 9.

The right region image obtaining unit 1 obtains a radiation image (three-dimensional radiation image) of the right region (for example, the right breast, right hand, right arm, or right leg) of almost symmetrical regions (for example, the breasts or extremities). The left region image obtaining unit 2 obtains a radiation image (three-dimensional radiation image) of the left region (for example, the left breast, left hand, left arm, or left leg) of the almost symmetrical regions.

The detection unit 3 detects at least one of the following: the position of a support unit which supports a region, the position of a compression unit which compresses the region, the position of an anatomical feature portion of the region, the position of a lesion portion of the region, the barycenter of the region, and the obtaining position (obtaining coordinates) of a radiation image. The anatomical feature portion includes a blood vessel branch portion, papilla, mammary gland, bone, and joint. For example, the detection unit 3 detects a three-dimensional feature position of the region (the position of an anatomical feature portion of the region, the position of a lesion portion of the region, the barycenter of the region, or the like).

The alignment unit 4 performs alignment between a radiation image of the right region and a radiation image of the left region based on these positions. For example, the alignment unit 4 performs alignment between a radiation image (three-dimensional radiation image) of the right region and a radiation image (three-dimensional radiation image) of the left region based on feature positions such as the position of an anatomical feature portion of the region, the position of a lesion portion of the region, and the barycenter of the region. The display control unit 5 causes a display unit (not shown) to display, on its screen, the radiation image of the right region and the radiation image of the left region, which have been aligned, upon arranging the images almost symmetrically.

Figure 2:
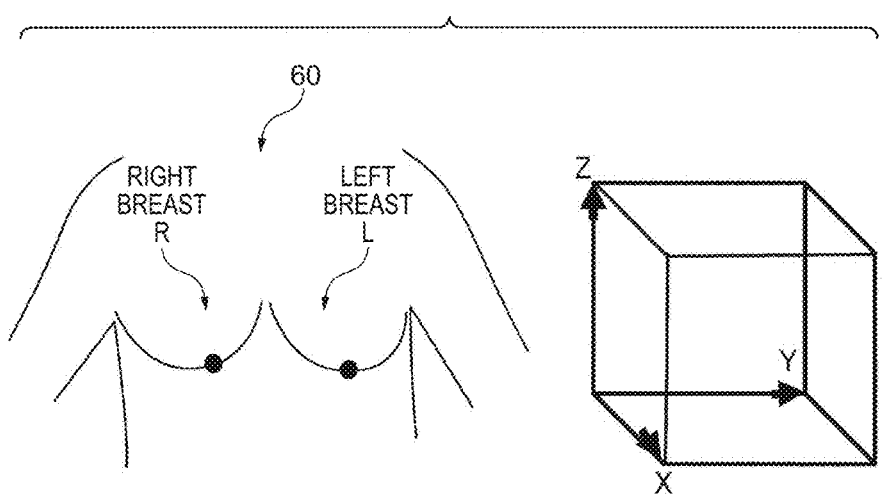
FIG. 2 is a view for explaining an axial section, a sagittal section, and a coronal section.

The image processing apparatus 101 according to this embodiment functions as a medical image processing apparatus and causes the display unit (not shown) to display axial tomographic images, sagittal tomographic images, coronal tomographic images, and three-dimensional images (three-dimensional radiation images such as CBCT images) of regions (for example, the breasts or extremities). The radiation imaging apparatus 102 obtains these radiation images. An axial section, a sagittal section, and a coronal section will be described with reference to FIG. 2. Assuming that the longitudinal direction, the transverse direction, and the body-axis direction are respectively defined as the X-axis, the Y-axis, and the Z-axis with respect to the trunk of an object 60, and an axial section, a sagittal section, and a coronal section are respectively defined as an X-Y plane, an X-Z plane, and a Y-Z plane.

Figure 3:
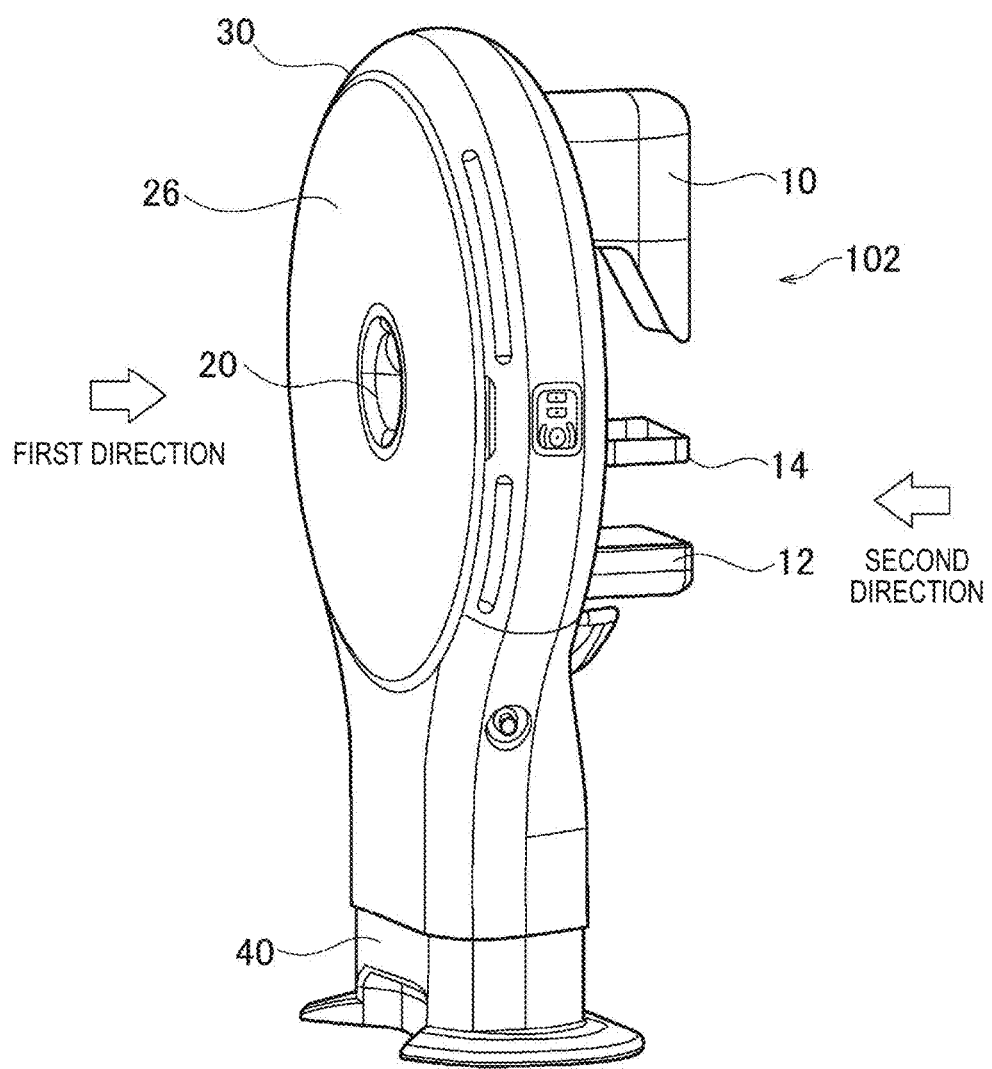
FIG. 3 is a first view showing an example of a radiation imaging apparatus.
Figure 4:
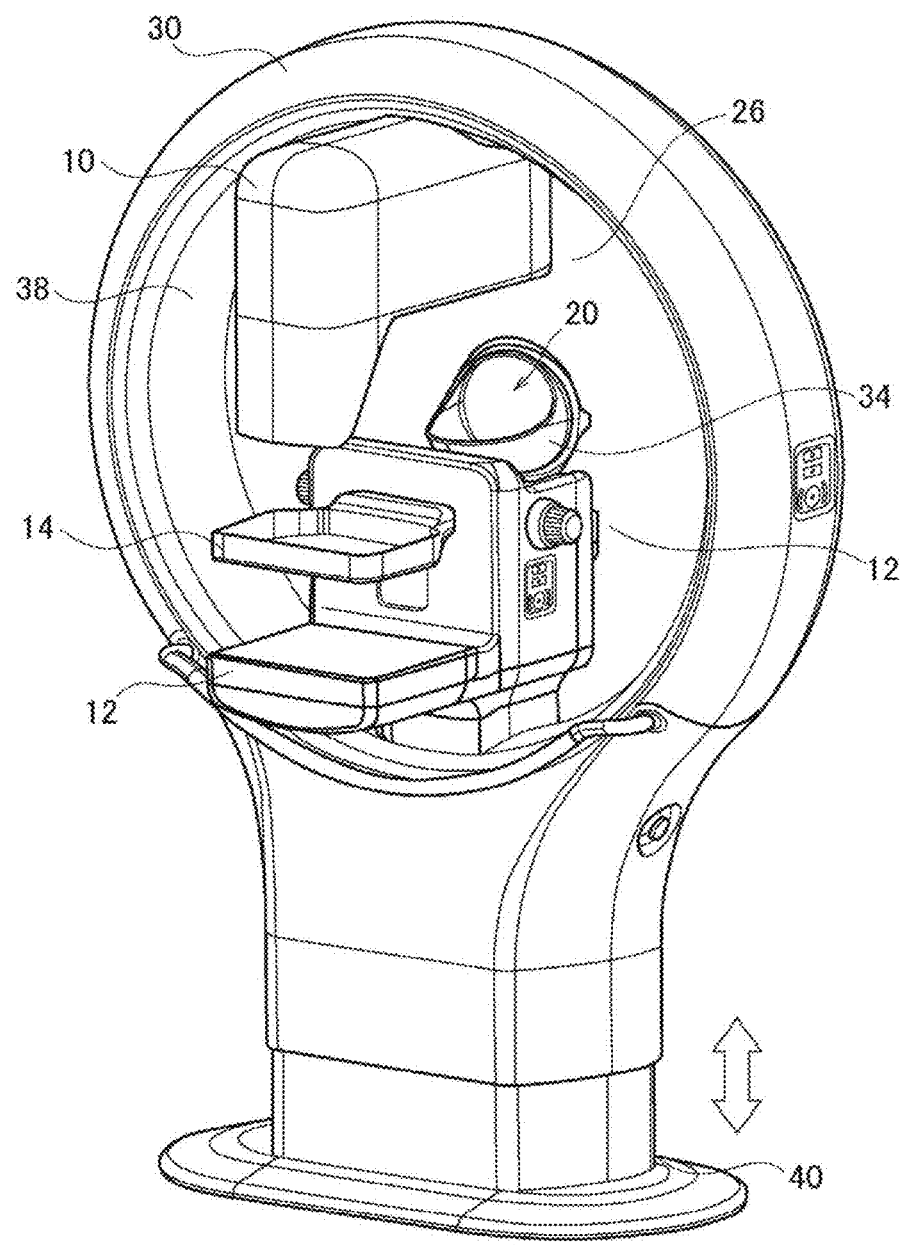
FIG. 4 is a second view showing an example of the radiation imaging apparatus.

FIGS. 3 and 4 are views showing an example of a radiation imaging apparatus. The radiation imaging apparatus 102 shown in FIGS. 3 and 4 performs CBCT imaging and mammography of the breasts of an object in a standing position. As shown in FIG. 3, the radiation imaging apparatus 102 includes a radiation generator 10, a radiation detection unit 12, a compression plate 14, an opening portion 20, a front cover 26, a gantry 30, and a leg portion 40. In addition, as shown in FIG. 4, the radiation imaging apparatus 102 includes a tray (support portion) 34 and a rotating frame 38.

In CBCT imaging, the breast is inserted into the opening portion 20 from the first direction and supported on the tray 34 so as to be arranged between the radiation generator 10 and the radiation detection unit 12. The opening portion 20 is formed in the central portion of the front cover 26.

The rotating frame 38 holds the radiation generator 10 and the radiation detection unit 12 and rotates along the inner circumferential of the circular portion of the gantry 30. When the rotating frame 38 rotates, the first imaging unit 8 (the radiation generator 10 and the radiation detection unit 12) obtains a radiation image (first radiation image) of the breast in a non-compressed state while rotating around the breast arranged from the first direction. Note that the first imaging unit 8 may obtain a three-dimensional radiation image while rotating the breast arranged from the first direction regardless of whether the breast is compressed or non-compressed. The radiation generator 10 generates radiation. The radiation detection unit 12 detects radiation transmitted through the breast.

The image processing apparatus 101 generates a radiation image (first radiation image) by reconstructing radiation image data detected by the radiation detection unit 12. The image processing apparatus 101 generates a radiation image (first radiation image) such as an axial tomographic image, sagittal tomographic image, coronal tomographic image, or three-dimensional image.

In mammography, the breast is compressed/arranged between the radiation detection unit 12 and the compression plate 14 from a second direction different from the first direction. The second imaging unit 9 (the radiation generator 10 and the radiation detection unit 12) obtains a radiation image (second radiation image) of the breast in a compressed state which is compressed/arranged from the second direction. The compression plate 14 is made of a transparent material which transmits radiation. When the compression plate 14 moves in the direction of the radiation detection unit 12, the breast is sandwiched and compressed/arranged between the compression plate 14 and the radiation detection unit 12. The radiation generator 10 generates radiation. The radiation detection unit 12 detects radiation transmitted through the breast.

The image processing apparatus 101 generates a radiation image (second radiation image) by reconstructing radiation image data detected by the radiation detection unit 12. The image processing apparatus 101 generates a radiation image (second radiation image) such as a craniocaudal tomographic image (CC image) or mediolateral oblique tomographic image (MLO image) in accordance with the direction of compression/arrangement of the breast. In addition, the image processing apparatus 101 generates a radiation image (second radiation image) such as a tomosynthesis image.

The first and second directions are almost perpendicular to a rotation plane of the front cover 26 or the rotating frame 38.

The right breast (right region) and the left breast (left region) are imaged. The right region image obtaining unit 1 obtains the radiation image of the right breast (right region). The left region image obtaining unit 2 obtains the radiation image of the left breast (left region).

Figure 5:
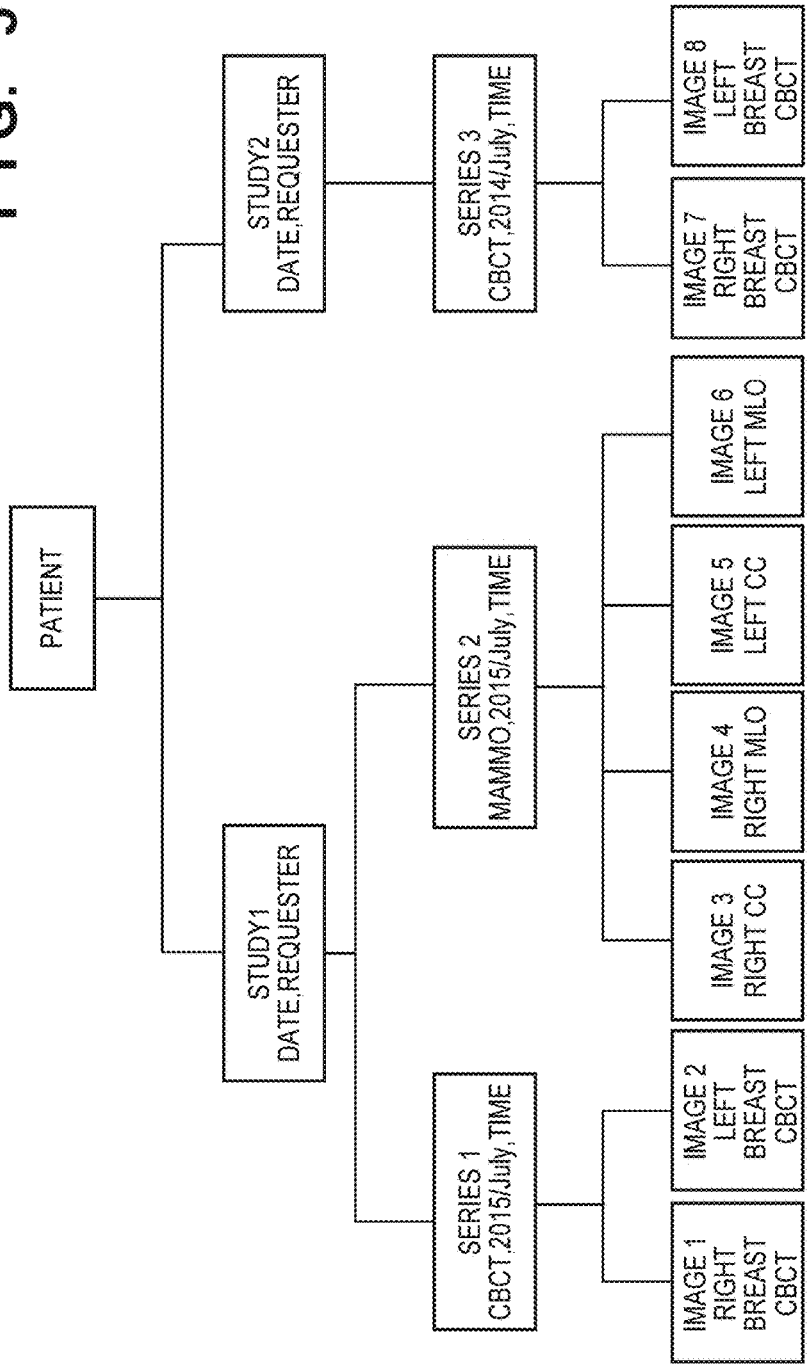
FIG. 5 is a block diagram showing an example of the hierarchical structure of radiation image data obtained by imaging.

FIG. 5 is a view showing an example of the hierarchical structure of radiation image data obtained by imaging. As shown in FIG. 5, the layers of the radiation image data are arranged such that patient data is located on the uppermost layer, and STUDY, SERIES, and IMAGES follow as lower layers in the order named. The radiation images (CBCT images) obtained by CBCT imaging are associated with (linked to) the radiation images (mammograms) obtained by mammography to allow the associated CBCT images and mammograms to be read out and displayed. For example, the CBCT images of the right and left breasts of the patient imaged in July 2015 are associated with the mammograms (CC images and MLO images) of the right and left breasts. In addition, the CBCT images of the right and left breasts of the patient imaged in July 2014 are associated with each other. The radiation images obtained in July 2015 are associated with the radiation images obtained in July 2014.

Figure 6:
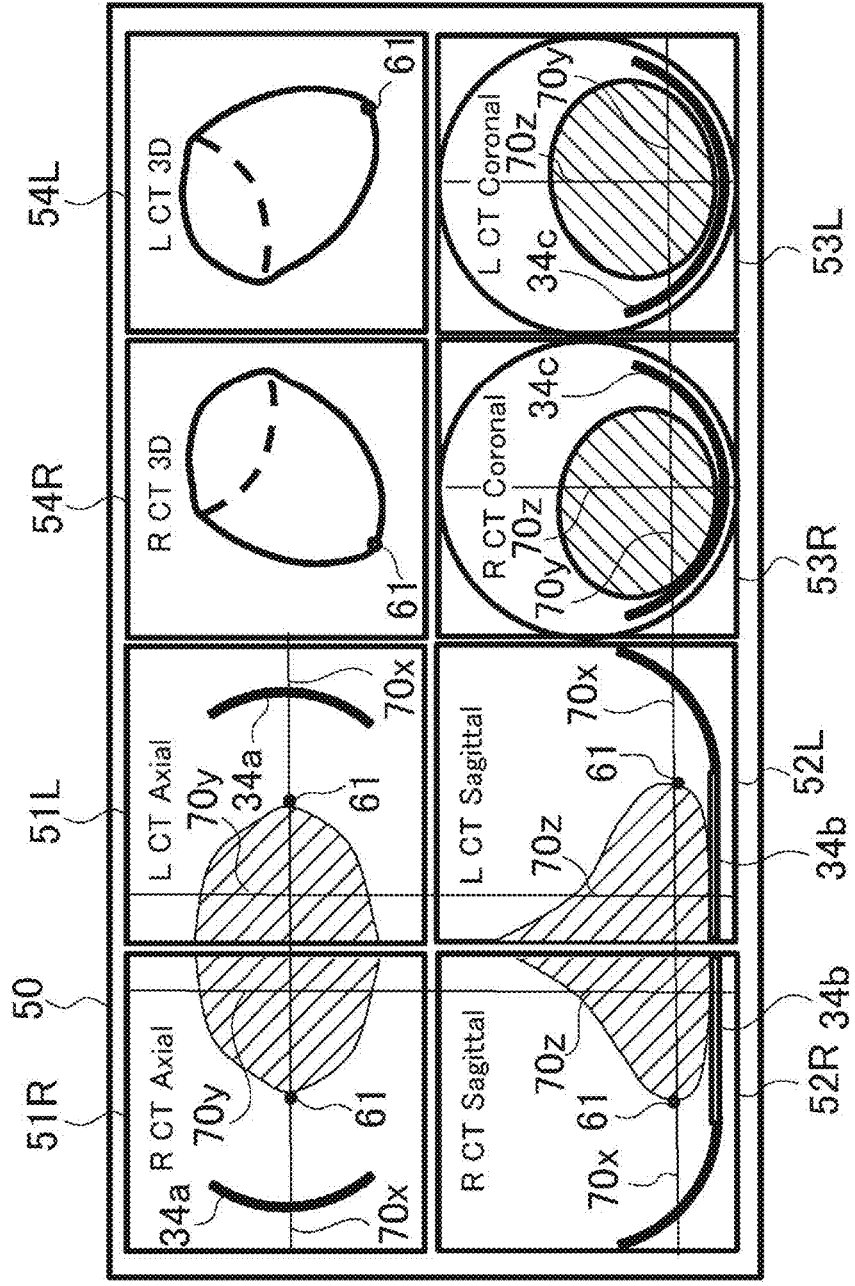
FIG. 6 is a view showing an example of the first layout pattern of first radiation images.

FIG. 6 is a view showing an example of a first layout pattern of CBCT images (radiation images) displayed by the display control unit 5 on the display unit. As shown in FIG. 6, the display control unit 5 causes the display unit to display a plurality of radiation images of a right breast (right region) R and a left breast (left region) L in FIG. 2 on a display screen 50, including axial tomographic images 51R and 51L, sagittal tomographic images 52R and 52L, coronal tomographic images 53R and 53L, and three-dimensional images 54R and 54L in the first layout pattern in which the respective pairs are arranged almost symmetrical to each other.

Note that when observing these images while facing the object, the radiation images 51R to 54R of the right region are displayed while being arranged on the left side, and the radiation images 51L to 54L of the left region are displayed while being arranged on the right side to make the object correspond to the placement of the right and left regions on the display screen 50.

The first layout pattern makes it possible to comparatively observe the CBCT images of the right and left regions. Comparing the right and left regions can improve the accuracy of detection of a lesion portion of the region.

The detection unit 3 detects at least one of the following: the position of the tray (support unit) 34 which supports the breast, the position of an anatomical feature portion (a blood vessel branch portion, papilla, mammary gland, or the like) of the breast, the position of a lesion portion (a calcified portion, tumor, or the like) of the breast, the barycenter of the breast, and the obtaining position (obtaining coordinates) of a radiation image.

The alignment unit 4 performs alignment between radiation images of the right breast and radiation images of the left breast based on the detected position. For example, the alignment unit 4 performs alignment between the axial tomographic images 51R and 51L, the sagittal tomographic images 52R and 52L, the coronal tomographic images 53R and 53L, and the three-dimensional images 54R and 54L so as to match the positions of papillae 61.

The alignment unit 4 may also perform alignment to match the axial tomographic images 51R and 51L, the sagittal tomographic images 52R and 52L, and the coronal tomographic images 53R and 53L with each other in terms of positions (including shapes) on tray sections 34a to 34c. In addition, the tray 34 may be provided with a marker for alignment between radiation images (including three-dimensional images).

In addition, the operation unit 6 may change the obtaining position of one of radiation images of the right breast (right region) R and the left breast (left region) L, and the display control unit 5 may change the obtaining position of the other radiation image in accordance with the change in the obtaining position of one radiation image. When the section position (obtaining position) of the coronal tomographic image 53R of the right breast R is changed after alignment between the coronal tomographic images 53R and 53L based on the positions of the papillae, the section position (obtaining position) of the coronal tomographic image 53L of the breast L is changed in conjunction with this operation.

Assume that an axial tomographic image 51, a sagittal tomographic image 52, a coronal tomographic image 53, and a three-dimensional image 54 are aligned with each other. In this case, when the section position (obtaining position) of one of the radiation images is changed by the operation unit 6, the section positions (obtaining positions) of the remaining radiation images are changed in conjunction with this change.

Note that the display control unit 5 may cause the display unit to display alignment axes $70x$ to $70z$ (for example, lines or cursors) on aligned radiation images. In addition, the display control unit 5 may cause the display unit to superimpose, on each three-dimensional image 54, a plane (for example, a transparent plane) corresponding to the section position of the three-dimensional image 54. In this case, as the operation unit 6 moves the alignment axes $70x$ to $70z$, the section positions (obtaining positions) of the radiation images change.

The display control unit 5 causes the display unit to display the radiation images 51R to 54R of the right breast and the radiation images 51L to 54L of the left breast, which have been aligned, upon arranging them almost symmetrically.

In this embodiment, the right and left regions are imaged one by one. According to the related art, since a medial image of overall right and left regions imaged by CT or MRI is displayed on a display unit (a liquid crystal display or the like), there is no need to perform alignment between images of the right and left regions separately imaged. Performing alignment is a feature of this embodiment.

The manner of deciding the geometrical positions of images of the right and left regions will be described with reference to FIGS. 7A and 7B. FIG. 7A is a view for explaining a case in which the right and left breasts are positioned with reference to the chest wall of a patient as a reference plane. The detection unit 3 can detect the papilla and the chest wall plane from the radiation image data of a three-dimensional image of the right breast. The chest wall plane image is defined as a Y-Z plane (X=0). When a contour is extracted by performing binarization processing of the chest wall plane image, a teardrop shape is generally extracted. The lengths of the teardrop shape (chest wall plane) in the Y-axis and Z-axis directions are calculated, and the midpoints of the respective lengths are respectively represented by "YcR" and "ZcR".

The detection unit 3 scans the Y-Z plane from a predetermined position "X=N−1" to "X=0" in the X-axis direction to detect, as the position of the papilla, the center of the breast section which is detected first. "N" represents the number of slices along the Y-Z plane of the radiation image data of the three-dimensional image. The position of the center of the breast section is decided by calculating the lengths of the breast section in the Y-axis and Z-axis directions and representing the midpoints of the respective lengths as "YnR" and "ZnR", respectively. When moving the Y-Z plane in the X-axis direction, a papilla position (XnR, YnR, ZnR) is decided by representing the X-axis position of a midpoint (YnR, ZnR) at which the breast section becomes almost minimum as "XnR".

In addition, the detection unit 3 may detect a mammary gland structure by analyzing a breast image from many sections, and detect the convergent point of the mammary gland structure as a papilla position. The detection unit 3 may also detect a papilla position by changing a threshold for the CT values of a three-dimensional image in consideration of the fact that the papilla is higher in CT value than fat and the mammary gland. Alternatively, the operation unit 6 may arbitrarily set a chest wall position and a papilla position, or the chest wall position and the papilla position detected by the detection unit 3 may be arbitrarily moved.

The chest wall position and papilla position of the left breast are decided in the same manner as the right breast. When deciding the chest wall position and papilla position of the left breast, the detection unit 3 may set the threshold for the binarization processing in deciding the chest wall position and papilla position of the right breast as an initial threshold for binarization processing of the left breast. This can shorten the detection time taken for a chest wall position and a papilla position.

As described above, the detection unit 3 detects the chest wall position (0, YcR, ZcR) and the papilla position (XnR, YnR, ZnR) of the right breast and the chest wall position (0, YcL, ZcL) and the papilla position (XnL, YnL, ZnL) of the left breast.

Referring to FIG. 7A, coordinates on a chest wall plane of the patient are expressed on an A-B plane. The A-B plane (chest wall plane) is, for example, a 35-cm square plane. The quantization unit of the A-B plane is 1 mm. Although the resolution of a three-dimensional image (three-dimensional radiation image) is 100 μm to 200 μm, the quantization of the chest wall position (0, YcR, ZcR) and the papilla position (XnR, YnR, ZnR) is matched with 1 mm.

In addition, it is possible to achieve a reduction in data capacity by matching the pixel size of a three-dimensional image with the quantization size of an A-B plane before calculating the chest wall position (0, YcR, ZcR) and the papilla position (XnR, YnR, ZnR), thereby speeding up the calculation of a chest wall position and a papilla position.

A method of associating (arranging) the right and left breasts with the A-B plane will be described with reference to FIG. 7A. A method of performing association with reference to a chest wall position and a method of performing association with reference to a papilla position will be described.

According to the method of performing association with reference to a chest wall position, the positional relationship between the right and left breasts is decided by setting a DBB (Distance Between Breasts) to 15 cm and the maximum length (maximum width) of the breast on the chest wall plane to 20 cm, and respectively aligning the right and left breasts with chest wall position (YcR, ZcR) of right breast= (10 cm, 17 cm) and chest wall position (YcL, ZcL) of left breast=(25 cm, 17 cm).

If the right and left breasts overlap (the DBB becomes less than 0) as the breast length (breast width) on the chest wall plane increases, the DBB may be set to a value larger than a set value (15 cm). The DBB may be set based on patient information of a chest radiation image (a chest X-ray image, chest CT image, or the like) of the patient.

The method of performing association with reference to a papilla position is used when a user (for example, a doctor) makes a diagnosis with reference to the papilla. The papilla position (XnR, YnR, ZnR) of the right breast and the papilla position (XnL, YnL, ZnL) of the left breast are obtained in the above manner.

The DBB is set to 15 cm, and the maximum length (maximum width) of the breast on the chest wall plane is set to 20 cm. The right and left breasts are respectively aligned with chest wall papilla position (0, YnR, ZnR)=(0 cm, 10 cm, 17 cm) obtained by projecting the right papilla position on the Y-Z plane (X=0) and chest wall papilla position (0, YnL, ZnL)=(0 cm, 25 cm, 17 cm) obtained by projecting the left papilla position on the Y-Z plane (X=0). As a result, the positional relationship between the right and left breasts is decided, and the positional relationship between the papillae is decided.

If the right and left breasts overlap (the DBB becomes less than 0) as the breast length (breast width) on the chest wall plane increases, the DBB may be set to a value larger than a set value (15 cm). In the above case, alignment is performed with respect to both the A-axis and the B-axis of the A-B plane. However, alignment may be performed with respect to either the A-axis or the B-axis.

The method of associating (arranging) the right and left breasts with a curved plane will be described with reference to FIG. 7B. Arranging the right and left breasts on a curved plane makes it possible to bring a medical image (a chest CT image, chest MRI image, or the like) of an object (for example, a patient) close to the actual breast placement based on object information (patient information). In addition, superimposing the right and left breasts within the same frame allows the user to make a diagnosis with a feeling close to reality.

Figure 7B:
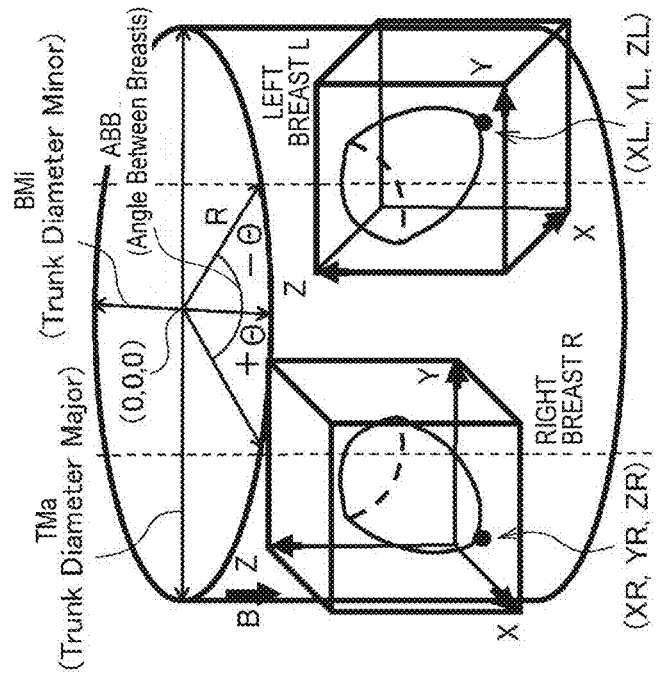
FIGS. 7A and 7B are views showing an example of alignment between right and left regions.
Figure 7A:
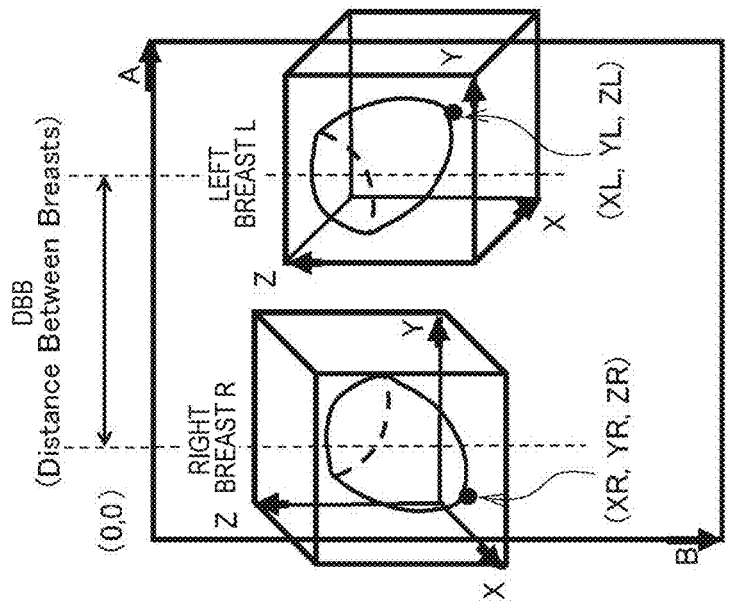

Referring to FIG. 7B, the trunk is approximated by an elliptic column, and the right and left breasts are arranged on a curved plane of the elliptic column. The right and left breasts are arranged in consideration of a TMa (Trunk Diameter Major), a TMi (Trunk Diameter Minor), and an ABB (Angle Between Breasts). Coordinates are expressed by polar coordinates (distance r, angle Θ, height B).

For example, the right and left breasts are arranged by setting the TMa, the TMi, and the ABB to 35 cm, 20 cm, and 30°, respectively. The position of the right breast is represented by (r, +Θ, b), and the position of the left breast is represented by (r, −Θ, b). Chest wall positions (0, YcR, ZcR) and (0, YcL, ZcL) are arranged with respect to the respective breast positions. The right breast is arranged at the angle "+Θ), and the left breast is arranged at the angle "−Θ".

Although the method of performing association with reference to chest wall positions has been described above, a method of performing association with reference to papilla positions can be implemented by obtaining papilla positions in the same manner as described above.

In the above manner, the alignment unit 4 performs alignment between a radiation image of the right breast and a radiation image of the left breast (FIG. 6). In addition, as the operation unit 6 changes the obtaining position of a radiation image, the obtaining positions of the radiation images of the right and left breasts are displayed on the display unit in conjunction with the change.

As described above, an obtaining position is changed by moving a cursor or the like. If, for example, the section position (obtaining position) of the coronal tomographic image 53R of the right breast R is changed, the section position (obtaining position) of the coronal tomographic image 53L of the left breast L is changed by the same distance in the same direction. In addition, since the breasts are almost symmetrical regions, when the section positions (obtaining positions) of the axial tomographic image 51R and the sagittal tomographic image 52R of the right breast R are changed, the section positions (obtaining positions) of the axial tomographic image 51L and the sagittal tomographic image 52L of the left breast L are changed by the same distance in the opposite direction.

Referring to FIG. 6, when the alignment axis 70y of the axial tomographic image 51R is moved in a direction away from the chest wall, the alignment axis 70y of the axial tomographic image 51L moves by the same distance in a direction away from the chest wall. Moving the alignment axis 70y will change the section positions (obtaining positions) of the coronal tomographic images 53R and 53L of the right and left breasts in conjunction with the movement.

In addition, when the alignment axis 70x of the axial tomographic image 51R is moved upward (in the right direction of the right breast), the alignment axis 70x of the axial tomographic image 51L moves upward (in the left direction of the left breast) by the same distance. Moving the alignment axis 70x will change the section positions (obtaining positions) of the sagittal tomographic images 52R and 52L of the right and left breasts in conjunction with the movement.

Figure 8:
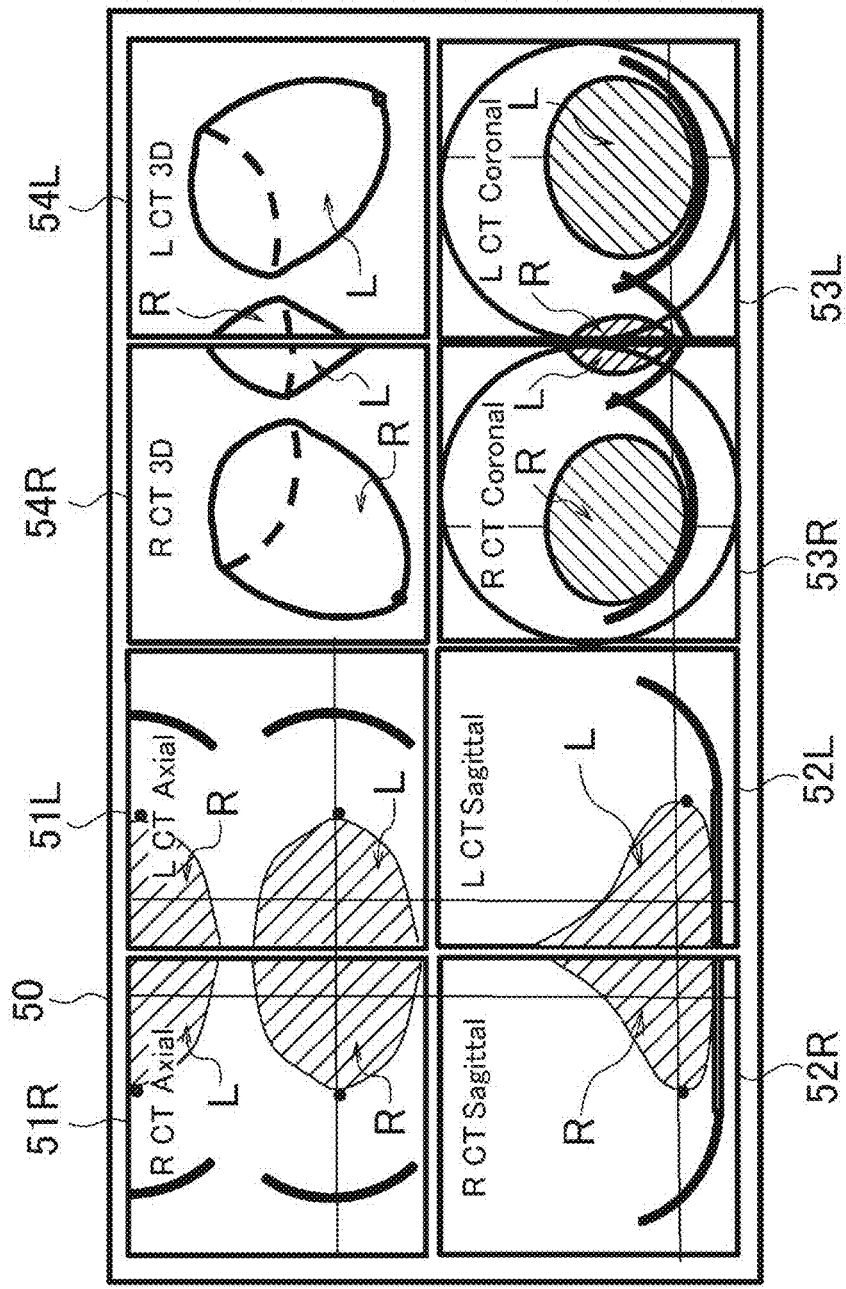
FIG. 8 is a view showing how the right and left regions are superimposed.

FIG. 8 is a view showing that images obtained by separately imaging the right breast (right region) and the left breast (left region) are superimposed on each other. The superimposing unit 7 superimposes aligned radiation images of the right breast (right region) and the left breast (left region) upon arranging them almost symmetrically. When the superimposed radiation images are reduced, since the positions of the radiation images (CBCT images) obtained by separately imaging the right and left breasts are associated with each other, the right and left breast images are superimposed within the same frame on the display unit.

When the axial tomographic image 51R is reduced in FIGS. 7A and 7B, the left breast L superimposed on the axial tomographic image 51R is displayed. In addition, the axial tomographic image 51L is reduced in conjunction with the reduction in the axial tomographic image 51R, and the right breast R superimposed on the axial tomographic image 51L is displayed. Likewise, in conjunction with the reduction in the axial tomographic image 51R, the coronal tomographic images 53R and 53L and the three-dimensional images 54R and 54L are reduced, and the other breast superimposed almost symmetrically is displayed.

When scrolling a radiation image as well as enlarging and reducing the radiation image, the other breast superimposed almost symmetrically is displayed. The operation unit 6 may switch between ON and OFF of superimposition of right and left regions.

Figure 9:
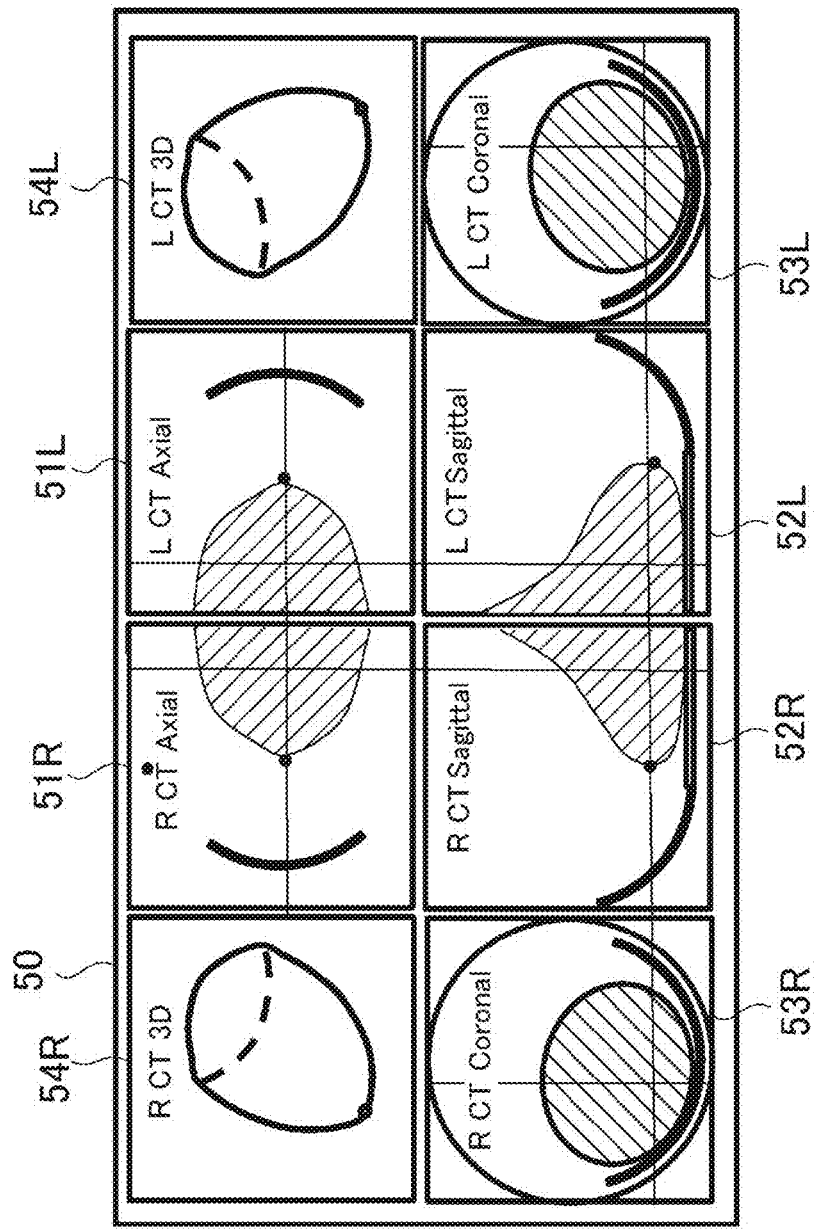
FIG. 9 is a view showing an example of the second layout pattern of first radiation images.

FIG. 9 is a view showing an example of a second layout pattern of CBCT images (radiation images) displayed by the display control unit 5. As shown in FIG. 9, the display control unit 5 causes the display unit to display, on the display screen 50, a plurality of radiation images of the right breast (right region) R, including the axial tomographic image 51R, the sagittal tomographic image 52R, the coronal tomographic image 53R, and the three-dimensional image 54R, and a plurality of radiation images of the left breast (left region) L, including the axial tomographic image 51L, the sagittal tomographic image 52L, the coronal tomographic image 53L, and the three-dimensional image 54L, in the second layout pattern in which they are arranged almost symmetrically.

The display control unit 5 comparatively displays radiation images of the right and left regions (axial tomographic images, sagittal tomographic images, coronal tomographic images, and three-dimensional images) almost symmetrically in an adjacent state as a whole.

The display control unit 5 may switch between the first layout pattern (FIG. 6) and the second layout pattern (FIG. 9). The first layout pattern places importance on the comparison between the respective sections of the right and left regions. The second layout pattern helps to three-dimensionally understand the respective regions. In the second layout pattern in FIG. 9, the axial tomographic images 51R and 51L and the sagittal tomographic images 52R and 52L are arranged almost symmetrically in the four middle frames. These tomographic images allow comparison between the sections of the right and left regions. As described above, the second layout pattern helps to three-dimensionally understand the respective regions and allows comparison between the sections of the right and left regions.

Figure 10:
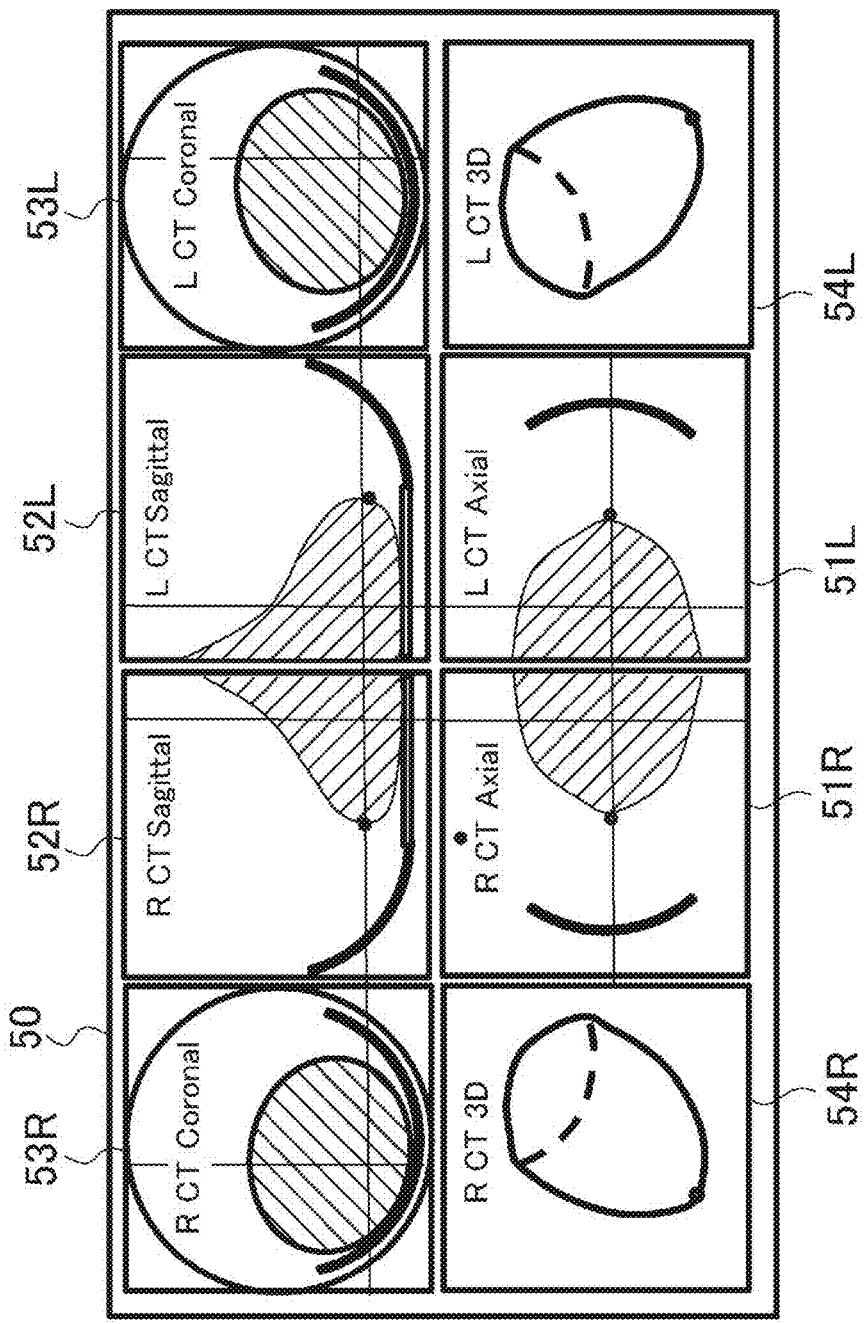
FIG. 10 is a view for explaining how radiation images are moved on a display screen.

FIG. 10 is a view for explaining how radiation images are moved on the display screen. The operation unit 6 moves the radiation images of one of the right breast (right region) and the left breast (left region) on the display screen 50. In accordance with the movement of the radiation images of one of the regions, the display control unit 5 moves and displays the radiation images of the other region on the display screen 50.

Referring to FIG. 10, the operation unit 6 interchanges the axial tomographic images 51R and 51L with the sagittal tomographic images 52R and 52L in the second layout pattern, and coronal tomographic images 53R and 53L with the three-dimensional images 54R and 54L. For example, the operation unit 6 includes a touch panel. When the user moves the axial tomographic image 51R on the touch panel with his/her finger, the axial tomographic image 51L moves in conjunction with this movement.

According to this embodiment, it is possible to associate radiation images (first radiation images) of the right and left regions, which are almost symmetrical, and display the radiation images of the right and left regions upon arranging them almost symmetrically.

Second Embodiment

The first embodiment has exemplified the radiation imaging system which displays first radiation images (for example, CBCT images) obtained by imaging almost symmetrical regions in a non-compressed state. The second embodiment will exemplify a radiation imaging system which displays first radiation images and second radiation images (for example, radiation images obtained by imaging in a compressed state, for example, mammograms and tomosynthesis images). Note that a description of the same arrangements, functions, and operations as those in the above embodiment will be omitted, and differences from the embodiment will be mainly described.

Figure 11:
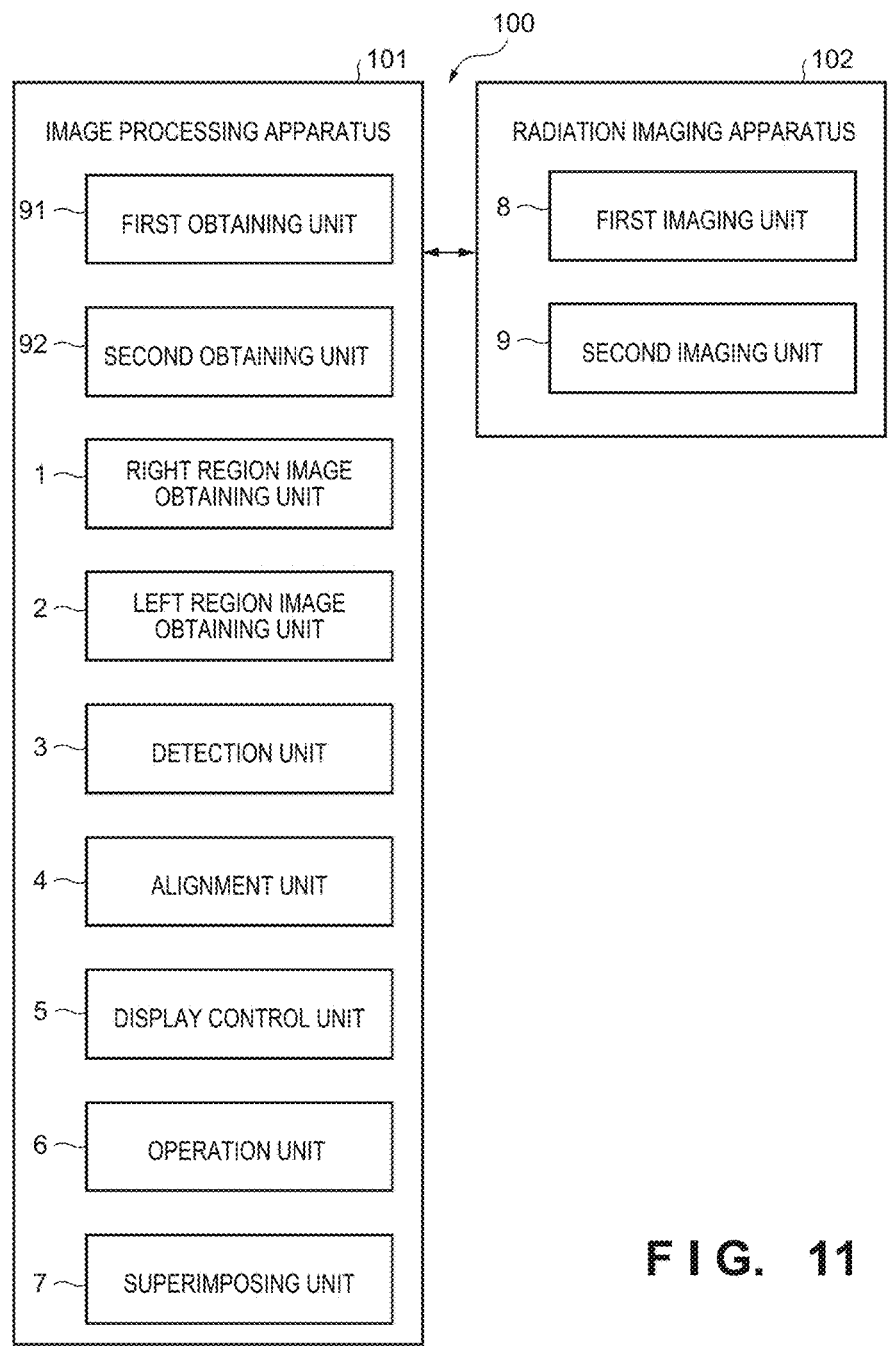
FIG. 11 is a block diagram showing an example of a radiation imaging system according to the second embodiment.

FIG. 11 is a view showing an example of the radiation imaging system according to this embodiment. An image processing apparatus 101 further includes a first obtaining unit 91 and a second obtaining unit 92. In the second embodiment, the first obtaining unit 91 obtains three-dimensional radiation images (first radiation images) of the almost symmetrical right and left regions (for example, the breasts or extremities) by imaging them. The second obtaining unit 92 obtains two-dimensional radiation images (second radiation images) of the almost symmetrical right and left regions by imaging them. In addition, the first obtaining unit 91 obtains the first radiation images by imaging almost symmetrical regions in a non-compressed state. The second obtaining unit 92 obtains the second radiation images by imaging the regions in a compressed state.

A first imaging unit 8 in FIGS. 3 and 4 (a radiation generator 10 and a radiation detection unit 12) obtains a radiation image (first radiation image) of the breast in a non-compressed state while rotating around the breast arranged from the first direction. Note that the first imaging unit 8 may obtain a three-dimensional radiation image while rotating the breast arranged from the first direction regardless of whether the breast is compressed. The first obtaining unit 91 obtains the obtained first radiation image.

A second imaging unit 9 (the radiation generator 10 and the radiation detection unit 12) obtains a radiation image (second radiation image) of the breast compressed/arranged from the second direction. Note that the second imaging unit 9 may obtain a two-dimensional radiation image compressed/arranged from the second direction different from the first direction regardless of whether the breast is compressed. The second obtaining unit 92 obtains the obtained second radiation image.

A right region image obtaining unit 1 obtains a two-dimensional image (first radiation image) of the right region from a three-dimensional radiation image of the right region. A left region image obtaining unit 2 obtains a two-dimensional image (first radiation image) of the left region from a three-dimensional radiation image of the left region. In addition, the right region image obtaining unit 1 obtains the first and second radiation images of the right region, and the left region image obtaining unit 2 obtains the first and second radiation images of the left region.

A detection unit 3 detects at least one of the following: the position of a support unit which supports a region, the position of a compression unit which compresses the region, the position of an anatomical feature portion of the region, the position of a lesion portion of the region, the barycenter of the region, the obtaining position of the first radiation image, and the obtaining position of the second radiation image.

If the region is the breast, the detection unit 3 detects at least one of the following: the position of a tray (support unit) 34 which supports the breast in FIG. 4, the position of an anatomical feature portion (a blood vessel branch portion, papilla, mammary gland, or the like) of the breast, the position of a lesion portion (a calcified portion, tumor, or the like) of the breast, the barycenter of the breast, and the obtaining position (obtaining coordinates) of a radiation image. For example, the detection unit 3 detects a three-dimensional feature position (the position of an anatomical feature portion of the region, the position of a lesion portion of the region, the barycenter of the region, or the like) of the region.

An alignment unit 4 performs alignment between the first radiation images of the right and left regions based on these positions, and then performs alignment between the second radiation images of the right and left regions. For example, the alignment unit 4 performs alignment between a radiation image (three-dimensional radiation image) of the right region and a radiation image (three-dimensional radiation image) of the left region based on feature positions such as the positions of anatomical feature portions of the regions, the position of the lesion portion of the region, and the barycenters of the regions.

In this manner, the alignment unit 4 associates the positions of three-dimensional radiation images of the right and left regions. In this case, the right region image obtaining unit 1 obtains a two-dimensional image of the right region from the associated three-dimensional radiation image of the right region. The left region image obtaining unit 2 obtains a two-dimensional image of the left region from the associated three-dimensional radiation image of the left region. In addition, the alignment unit 4 may perform alignment between the first radiation image and the second radiation image of at least one of the right and left regions based on these positions.

A display control unit 5 causes the display unit to display the first radiation images which are the two-dimensional images of the right and left regions and obtained from the three-dimensional images of the right and left regions and the second radiation images which are the two-dimensional radiation images of the right and left regions, upon arranging them symmetrically. In addition, the display control unit 5 causes the display unit to display the aligned first radiation images of the right and left regions upon arranging them almost symmetrically, and to display the aligned second radiation images of the right and left regions upon arranging them almost symmetrically.

FIGS. 12A and 12B and FIGS. 13A and 13B are views for explaining alignment between the first radiation image (CBCT image) and the second radiation image (mammogram). In this embodiment, as described with reference to FIG. 7A, the first radiation images of the right and left breasts are associated with an A-B plane. Thereafter, the second radiation image (mammogram) is associated with the first radiation image (CBCT image). A chest wall position and a papilla position are detected by performing binarization processing or the like for the second radiation image (mammogram). The first and second radiation images are associated with each other with reference to the chest wall position or papilla position.

Figure 12A:
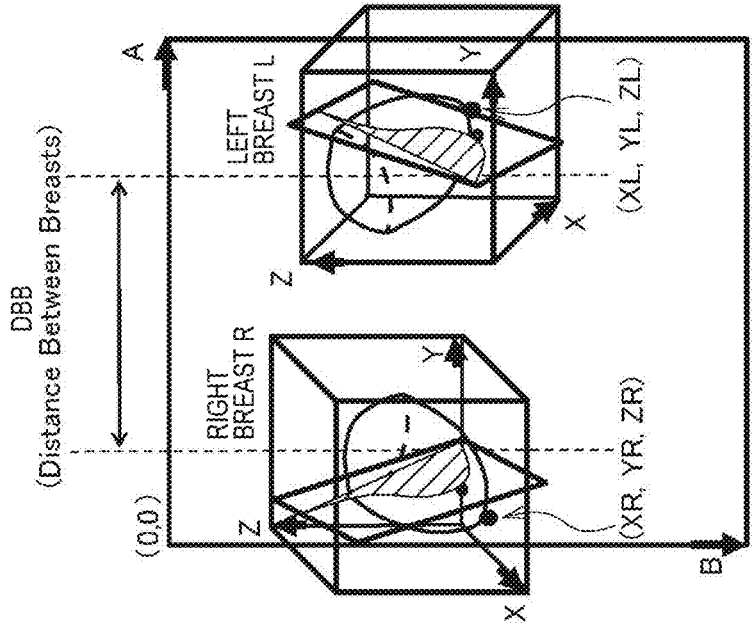
FIGS. 12A and 12B are first views for explaining alignment between a first radiation image and a second radiation image.
Figure 13A:
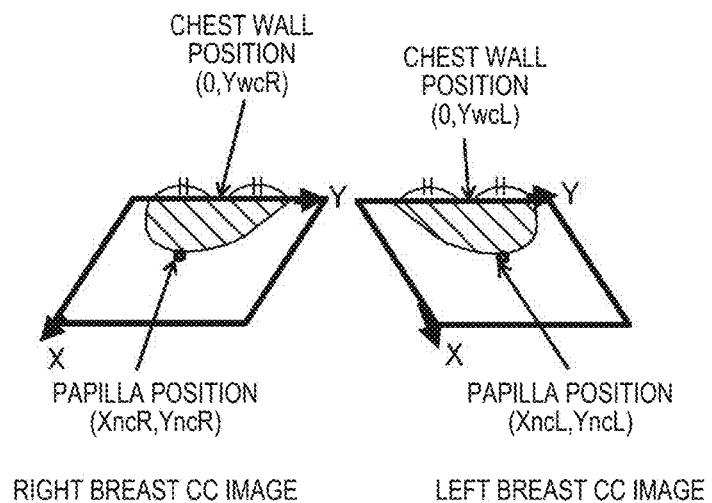
FIGS. 13A and 13B are second views for explaining alignment between the first radiation image and the second radiation image.

FIGS. 12A and 13A are views for explaining how a CC image obtained by mammography is associated with the first radiation image (CBCT image). A case in which they are associated with each other with reference to the chest wall position will be described with reference to FIGS. 12A and 13A. The alignment unit 4 associates a chest wall position (0, YwcR) as a midpoint of the chest wall plane of the second radiation image (two-dimensional CC image) of the right breast with a chest wall position (0, YcR, ZcR) of the first radiation image (three-dimensional CT image or the like) of the right breast.

When performing association with reference to the papilla position, the alignment unit 4 associates a chest wall papilla position (0, YncR) obtained by projecting a papilla position (XncR, YncR) on the Y-axis (X=0) with a chest wall papilla position (0, YnR, ZnR) obtained by projecting a papilla position (XnR, YnR, ZnR) of the first radiation image of the right breast on the Y-Z plane (X=0) (YnR=YncR). With regard to the left breast, as in the case of the right breast, the first and second radiation images are associated with each other with reference to the chest wall position (or the papilla position).

Figure 12B:
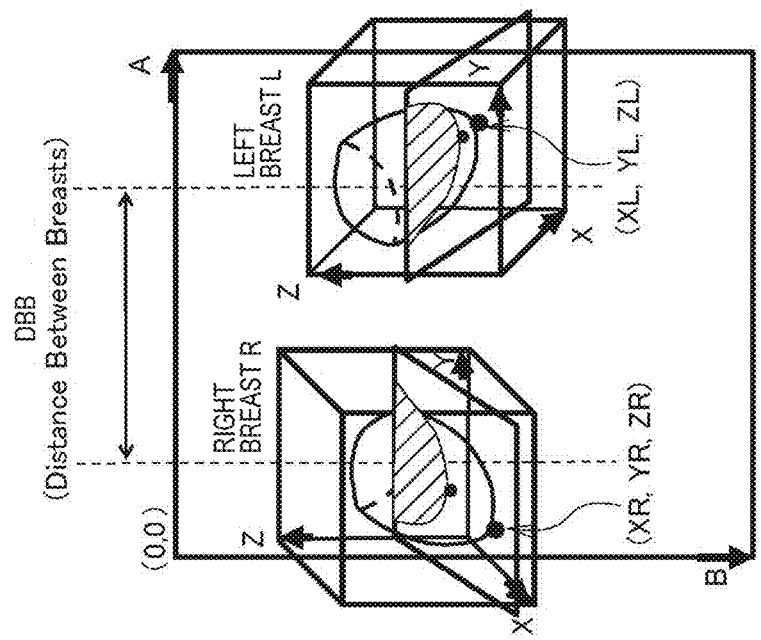
Figure 13B:
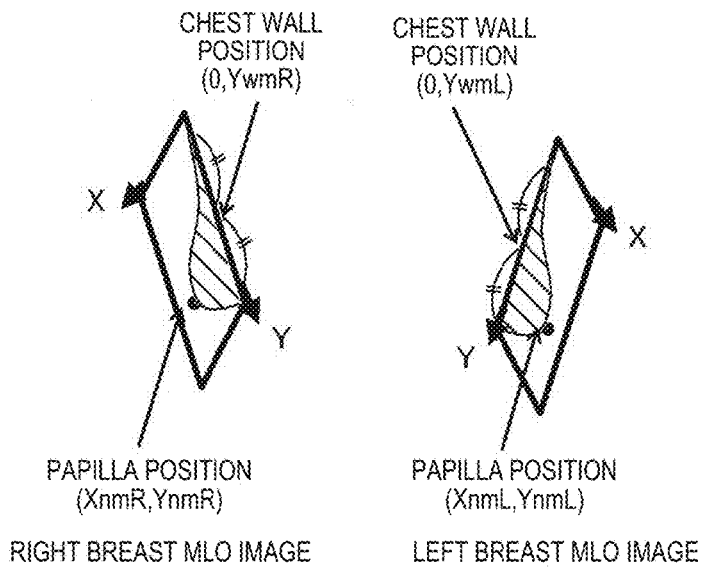

FIGS. 12B and 13B are views for explaining how an MLO image obtained by mammography is associated with the first radiation image (CBCT image). The alignment unit 4 associates a chest wall position (0, YwmR) as a midpoint of the chest wall plane of the second radiation image (two-dimensional MLO image) of the right breast with a chest wall position (0, YcR, ZcR) of the first radiation image (three-dimensional CT image or the like) of the right breast (YcR=YwmR).

When performing association with reference to the papilla position, the alignment unit 4 associates a chest wall papilla position (0, YnmR) obtained by projecting a papilla position (XnmR, YnmR) of the second radiation image of the right breast on the Y-axis (X=0) with a chest wall papilla position (0, YnR, ZnR) obtained by projecting a papilla position (XnR, YnR, ZnR) of the first radiation image of the right breast on the Y-Z plane (X=0).

With regard to the left breast, as in the case of the right breast, the first and second radiation images are associated with each other with reference to the chest wall position (or the papilla position). In addition, when aligning an MLO image, the alignment unit 4 aligns the MLO image with the first radiation image in accordance with a tilt (for example, 60°) in the mediolateral oblique direction at the time of obtaining the MLO image, as well as performing alignment with reference to a chest wall position or papilla position.

In this manner, the alignment unit 4 performs alignment between the radiation image of the right breast and the radiation image of the left breast. As an operation unit 6 changes the obtaining position of a radiation image, the display unit displays the obtaining positions of the radiation images of the right and left breasts in conjunction with the change.

Figure 14:
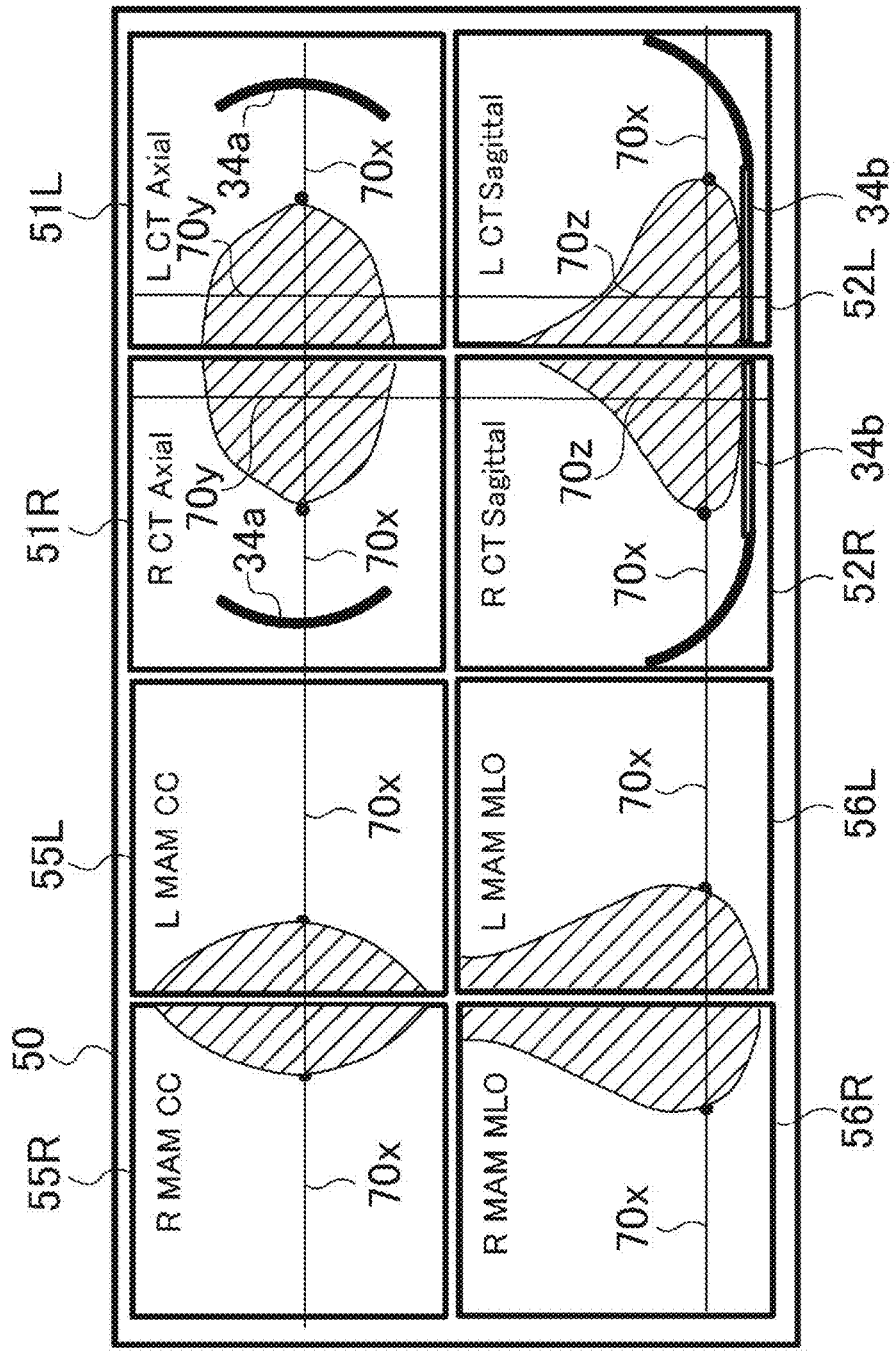
FIG. 14 is a view showing an example of the first layout pattern of the first and second radiation images.

FIG. 14 is a view showing an example of the first layout pattern of CBCT images (first radiation images) and mammograms (second radiation images) displayed by the display control unit 5. As shown in FIG. 14, the display control unit 5 arranges axial tomographic images 51R and 51L and sagittal tomographic images 52R and 52L (first radiation images) of the right breast (right region) and the left breast (left region) almost symmetrically. In addition, the display control unit 5 causes the display unit to display CC images 55R and 55L and MLO images 56R and 56L (second radiation images) of the right breast (right region) and the left breast (left region) in the first layout pattern in which the respective pairs are arranged almost symmetrical to each other.

Figure 15:
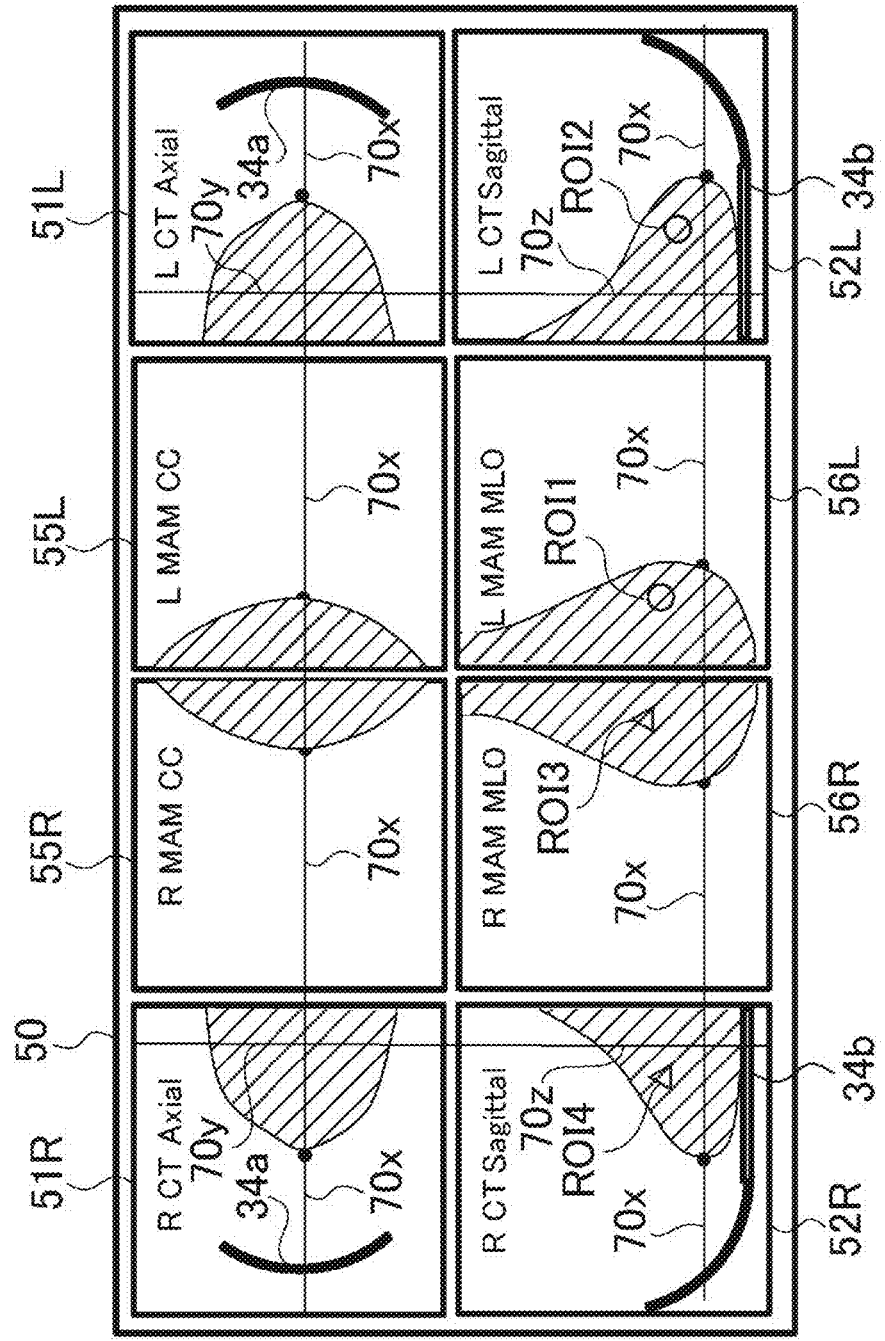
FIG. 15 is a view showing an example of the second layout pattern of the first and second radiation images.

FIG. 15 is a view showing an example of the second layout pattern of CBCT images (first radiation images) and mammograms (second radiation images) displayed by the display control unit 5. As shown in FIG. 15, the display control unit 5 causes the display unit to display the first and second radiation images (the axial tomographic image 51R, the sagittal tomographic image 52R, the CC image 55R, and the MLO image 56R) of the right breast (right region) and the first and second radiation images (the axial tomographic image 51L, the sagittal tomographic image 52L, the CC image 55L, and the MLO image 56L) of the left breast (left region) in the second layout pattern in which they are arranged almost symmetrically.

The display control unit 5 comparatively displays radiation images of the right and left regions (axial tomographic images, sagittal tomographic images, coronal tomographic images, and three-dimensional images) almost symmetrically in an adjacent state as a whole.

Referring to FIGS. 14 and 15, the alignment unit 4 associates three-dimensional CT images (first radiation images) corresponding to two-dimensional mammograms (second radiation images) of the right and left breasts. In this case, the axial tomographic images 51R and 51L and the sagittal tomographic images 52R and 52L display sections near the display CC images 55R and 55L and the MLO images 56R and 56L.

When the first radiation images are to display sections near the second radiation images, they can be displayed by performing RAYSUM processing or MIP processing.

In addition, when the operation unit 6 sets a region of interest ROI1 in the MLO image 56L of the left breast, a region of interest ROI2 with a correlation with the region of interest ROI1 being equal to or more than a predetermined threshold may be selected, and the sagittal tomographic image 52L including the selected region of interest ROI2 may be displayed. After the sagittal tomographic image 52L of the left breast is decided, the sagittal tomographic image 52R of the right breast associated with the sagittal tomographic image 52L is displayed.

Note that a correlation may be calculated by using pattern matching. In this case, while a slice image on the X-Z plane is moved in the slice direction, a product-sum operation is performed near the region of a slice image corresponding to the position of the region of interest ROI1 in the MLO image 56L. A slice image equal to or more than a predetermined threshold for product-sum values is displayed as the sagittal tomographic image 52L. In addition, if the first radiation image (three-dimensional CT image) and the second radiation image (two-dimensional mammogram) differ in pixel size, it is necessary to match the pixel size of the first radiation image with that of the second radiation image by converting the pixel size difference and calculate a correlation.

When the operation unit 6 sets a region of interest ROI3 in the MLO image 56R of the right breast, a region ROI4 with a correlation with the region of interest ROI4 being equal to or more than a predetermined threshold is selected, and the sagittal tomographic image 52R including the selected region ROI4 may be displayed. In this case, after the sagittal tomographic image 52R of the right breast is decided, the sagittal tomographic image 52L of the left breast associated with the sagittal tomographic image 52R is displayed.

As each of the regions of interest ROI1 and ROI3, the position of an anatomical feature portion (a blood vessel branch portion, papilla, mammary gland, or the like) of the breast, a lesion portion (a calcified portion, tumor, MASS, or the like) of the breast, or the like is selected.

Although the sagittal tomographic images 52R and 52L are tomographic images on the X-Z plane, tomographic images (first radiation images) based on a tilt in the mediolateral oblique direction at the time of obtaining an MLO image may be reconstructed from radiation imaged data and displayed in place of the sagittal tomographic images 52R and 52L.

The display control unit 5 may switch between the first layout pattern (FIG. 14) and the second layout pattern (FIG. 15). The first layout pattern places importance on comparison between the respective sections of the left and right regions. The second layout pattern helps to three-dimensionally understand the respective regions. In the second layout pattern in FIG. 15, the display CC images 55R and 55L and the MLO images 56R and 56L are arranged almost symmetrically in the four middle frames. These tomographic images allow comparison between the sections of the right and left regions. As described above, the second layout pattern helps to three-dimensionally understand the respective regions and allows comparison between the sections of the right and left regions.

In addition, the operation unit 6 may move one of radiation images of the right breast (right region) and the left breast (left region) on a display screen 50, and the display control unit 5 may display the other radiation image on the display screen 50 upon moving it in accordance with the movement of one radiation image. A superimposing unit 7 may superimpose the aligned radiation images of the right breast (right region) and the left breast (left region) upon arranging them almost symmetrically. In addition, the superimposing unit 7 may superimpose the aligned first radiation image (the axial tomographic image, sagittal tomographic image, coronal tomographic image, three-dimensional image, or the like) and second radiation imaging (the CC image, MLO image, tomosynthesis image, or the like).

Figure 16:
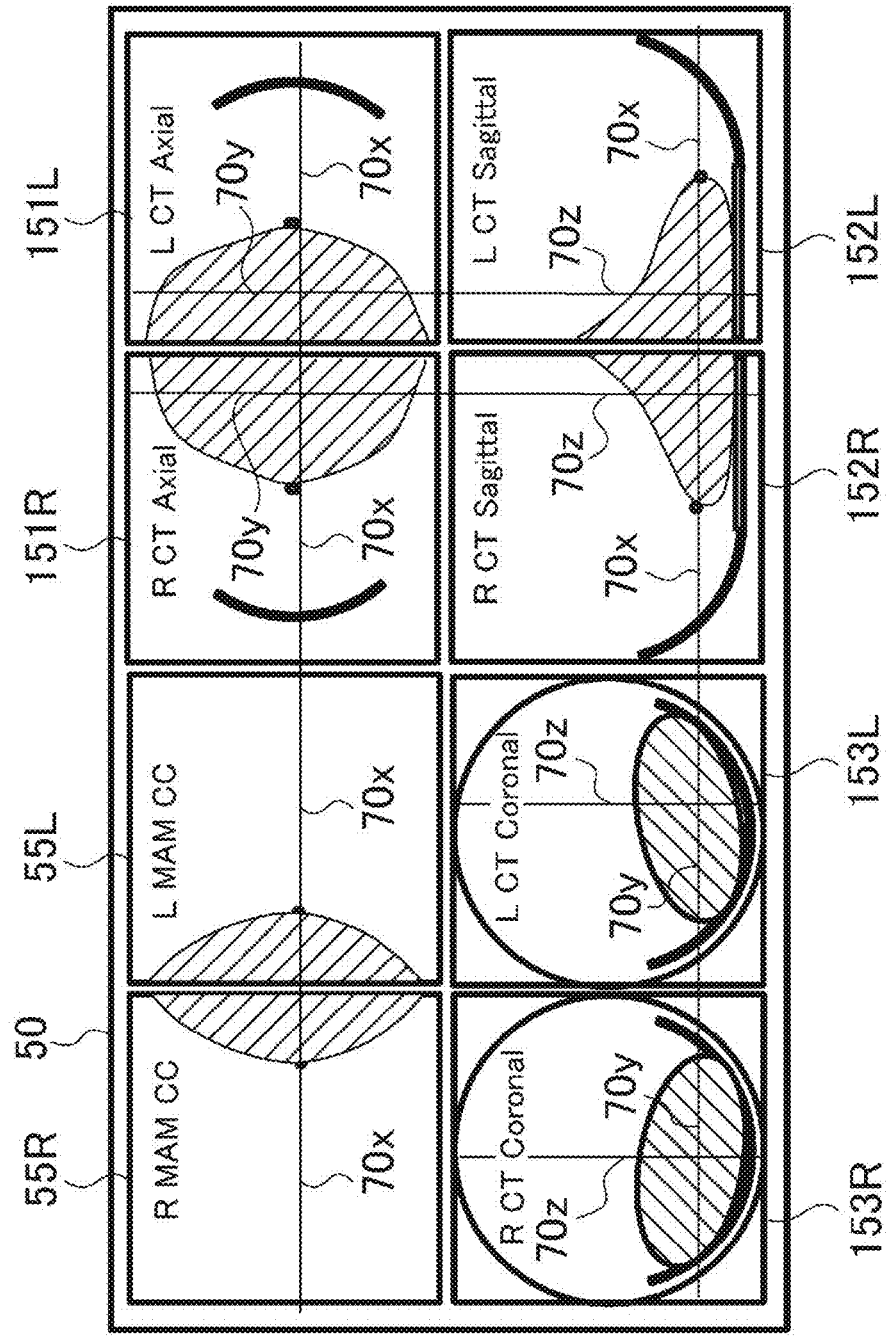
FIG. 16 is a view for explaining the deformation of the first radiation image in the compressing direction of a CC image.

FIG. 16 is a view for explaining how radiation images (first radiation images) in a non-compressed state are deformed into radiation images (CC images) in a compressed state. The display control unit 5 deforms the first radiation images in the compressing direction of the second radiation images and causes the display unit to display the resultant images. In addition, the display control unit 5 may deform the shape of a region in one of the aligned first and second radiation images so as to approximate the shape of a region in the other image and cause the display unit to display the resultant image.

Note that as shown in FIG. 15, when the operation unit 6 sets the regions of interest ROI1 and ROI3 in the second radiation images to calculate the correlation between the first and second radiation images, the first radiation images may be deformed. The image processing apparatus 101 may further include a deforming unit to deform radiation images.

A compression model is applied to the deformation of a radiation image. For example, as shown in FIG. 17, affine transformation is used as a compression model. Note that as the compression degree of a compression model, the compression force of a compression plate 14 or a change in breast thickness before and after compression may be used. In addition, a radiation image may be deformed in a direction perpendicular to the compressing direction in consideration of a Poisson ratio.

For example, the chest wall position and the papilla position of each first radiation image (three-dimensional image) affine-transformed in the compressing direction are calculated. The alignment unit 4 then performs alignment between the first and second radiation images with reference to the chest wall position or papilla position. After the alignment, the first radiation images deformed in the compressing direction are displayed as axial tomographic images 151R and 151L, sagittal tomographic images 152R and 152L, and coronal tomographic images 153R and 153L.

Figure 18:
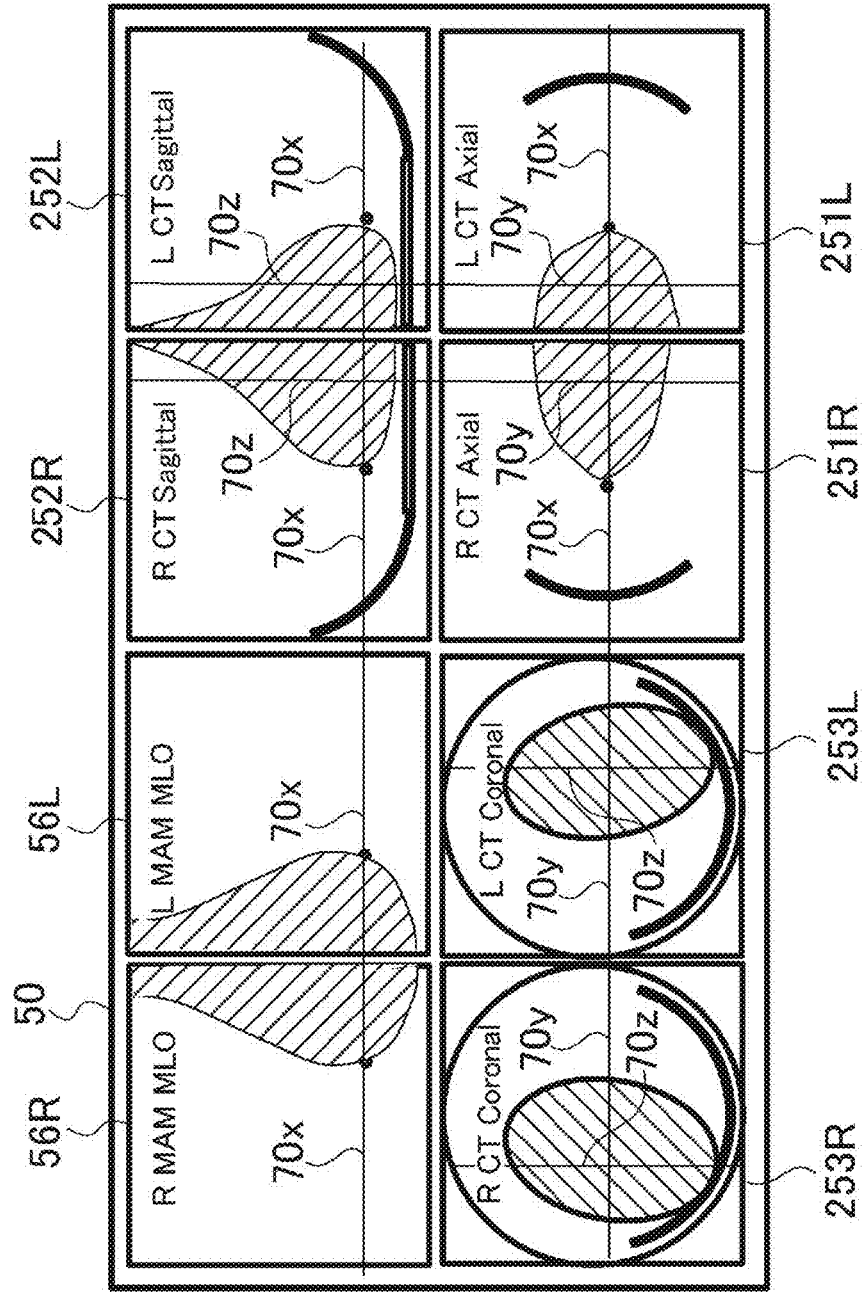
FIG. 18 is a view for explaining the deformation of the first radiation image in the compressing direction of an MLO image.
Figure 19:
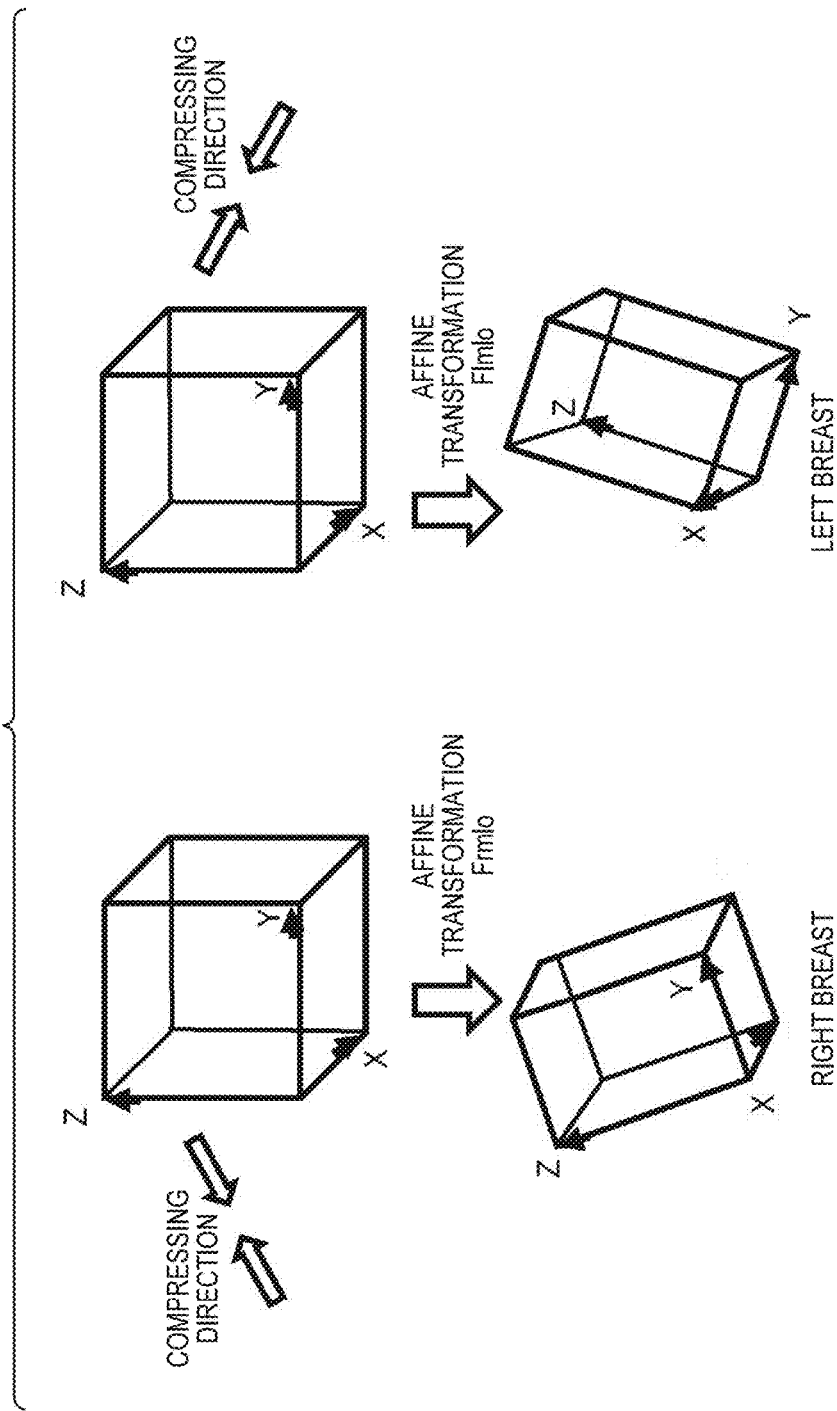
FIG. 19 is a view how affine transformation is used as a compression model.

FIG. 18 is a view for explaining how radiation images (first radiation images) in a non-compressed state are deformed in the compressing direction of radiation images (MLO images) in a compressed state. A compression model is applied to the deformation of a radiation image. For example, as shown in FIG. 19, affine transformation is used as a compression model. Note that as the compression degree and compression angle of a compression model, the compression force of the compression plate 14, a change in breast thickness before and after compression, or a tilt (for example, 60°) in the mediolateral oblique direction at the time of obtaining the MLO image, and the like may be used. In addition, a radiation image may be deformed in a direction perpendicular to the compressing direction in consideration of a Poisson ratio.

For example, a chest wall position and a papilla position in each first radiation image (three-dimensional image) affine-transformed in the compressing direction are calculated. The alignment unit 4 then performs alignment between the first and second radiation images with reference to the chest wall position or papilla position. After the alignment, the first radiation images deformed in the compressing direction are displayed as axial tomographic images 251R and 251L, sagittal tomographic images 252R and 252L, and coronal tomographic images 253R and 253L.

According to this embodiment, it is possible to display radiation images (first radiation images) obtained by imaging almost symmetrical regions in a non-compressed state and radiation images (second radiation images) obtained by imaging the regions in a compressed state in association with each other.

The embodiment described above can be changed and modified as follows.

For example, the alignment unit 4 may perform alignment between radiation images obtained at the first time and radiation images obtained at the second time based on positions detected by the detection unit 3. In this case, the display control unit 5 causes the display unit to display the aligned radiation images obtained at the first and second times upon arranging them almost symmetrically.

Figure 20:
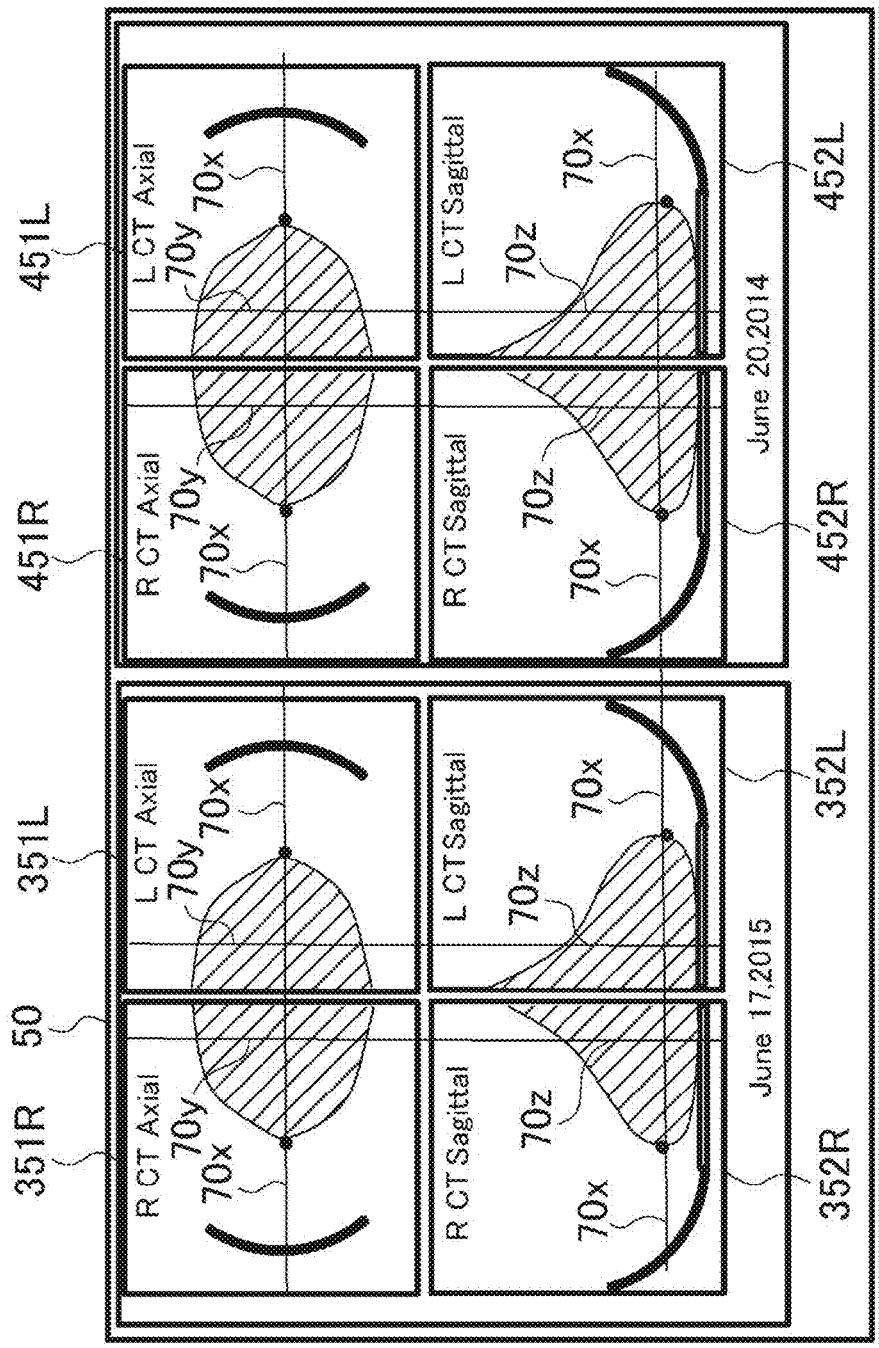
FIG. 20 is a view for explaining alignment between radiation images obtained at first and second times.

FIG. 20 is a view for explaining alignment between radiation images obtained at the first time (Jun. 17, 2015) and radiation images obtained at the second time (Jun. 20, 2015). As shown in FIG. 20, axial tomographic images 351R and 351L and sagittal tomographic images 352R and 352L obtained at the first time (Jun. 17, 2015) and axial tomographic images 451R and 451L and sagittal tomographic images 452R and 452L obtained at the second time (Jun. 20, 2015) are almost symmetrically and comparatively displayed.

Third Embodiment

Imaging apparatuses such as CT (Computed Tomography) and MRI (Magnetic Resonance Imaging) apparatuses generate three-dimensional image data by performing imaging from different angles. An image display apparatus displays tomographic images based on three-dimensional image data obtained by an imaging apparatus.

Japanese Patent Laid-Open No. 2011-224355 discloses a method of generating comparative images of the right and left breasts by cutting tomographic images of sagittal sections from three-dimensional image data and rotating and combining two images equidistant from the center of an apparatus coordinate system in the lateral direction. Japanese Patent Laid-Open No. 2013-85560 discloses a method of specifying papilla areas of the right and left breasts and displaying MPR images upon laterally juxtaposing them on the two sides of a median plane.

In general, an operator (doctor) who diagnoses the breasts performs diagnosis by comparing the different structures, densities, and the like of the right and left breasts displayed on a display apparatus. In this case, when using the method disclosed in Japanese Patent Laid-Open No. 2011-224355, it is sometimes difficult to display images to be compared side by side if the center of the object does not coincide with the lateral center of the apparatus coordinate system. In addition, when using the method disclosed in Japanese Patent Laid-Open No. 2013-85560, it is sometimes difficult to generate symmetrical images by using one axis if the tilts of the respective breasts differ from each other because of the influence of the body posture at the time of imaging each breast.

The following embodiment will exemplify a technique of facilitating comparative observation of tomographic images.

Fourth Embodiment

Figure 21A:
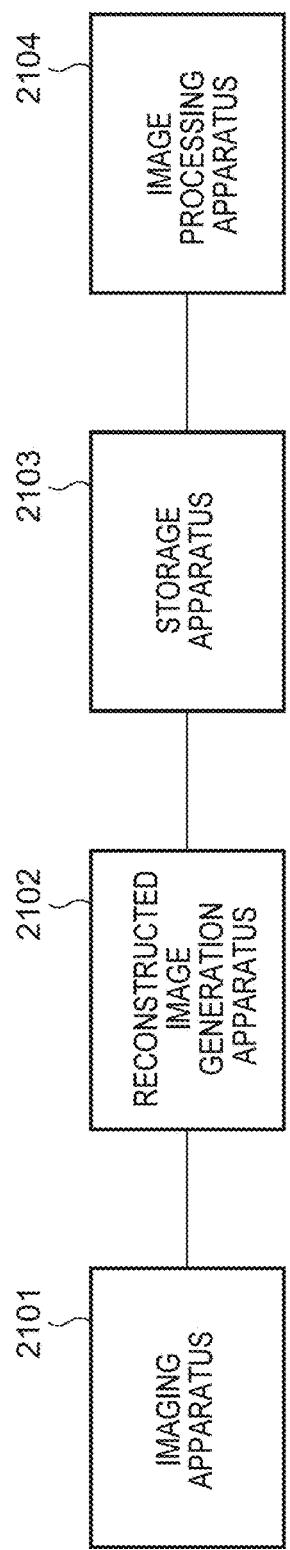
FIGS. 21A and 21B are functional block diagrams showing the arrangements of an image display system 2100 and an image processing apparatus 2104.

FIG. 21A is a block diagram showing the arrangement of an image display system according to the fourth embodiment. An image display system 2100 includes an imaging apparatus 2101, a reconstructed image generation apparatus 2102, a storage apparatus 2103, and an image processing apparatus 2104. The imaging apparatus 2101 is an imaging apparatus such as a CT (Computed Tomography) apparatus or MRI (Magnetic Resonance Imaging) apparatus.

Figure 21B:
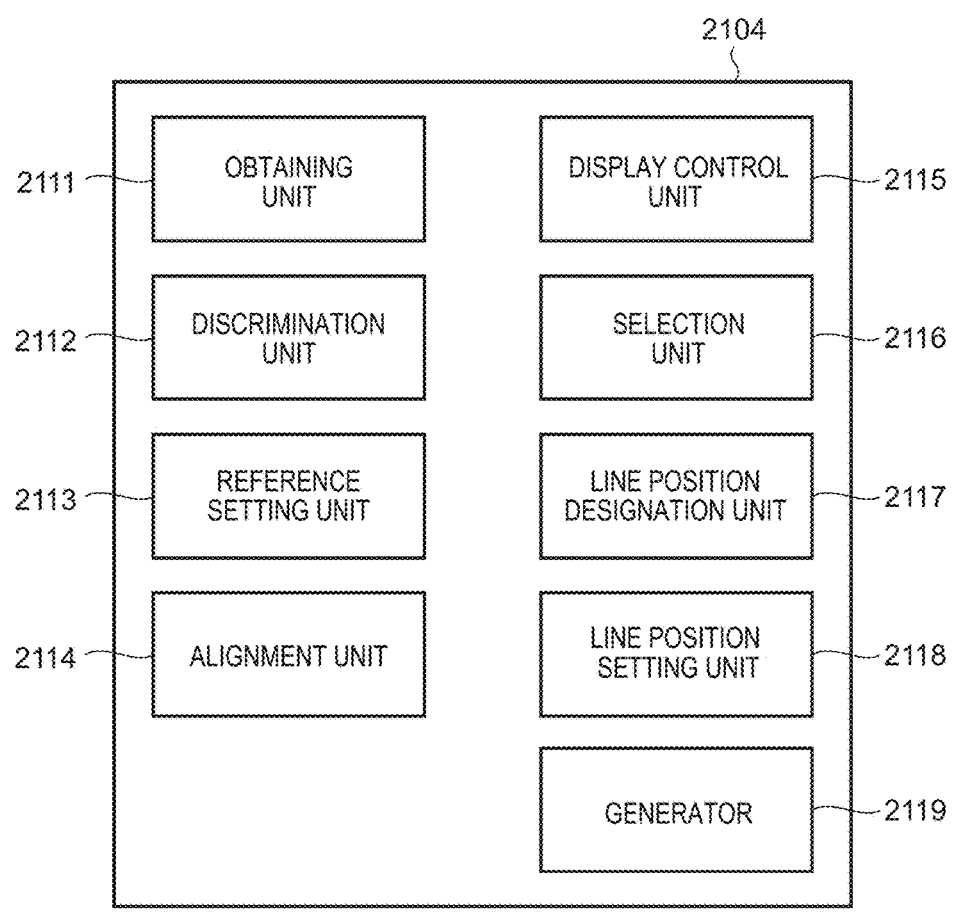
Figure 22:
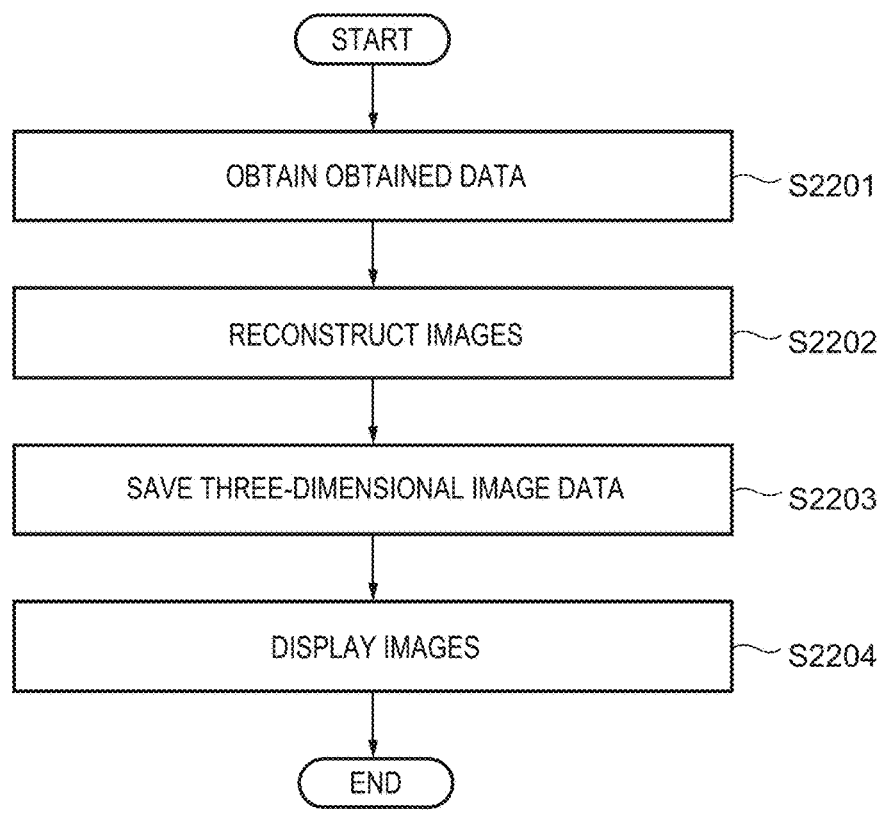
FIG. 22 is a flowchart showing processing by the image display system 2100.

FIG. 22 is a flowchart showing processing by the image display system according to this embodiment. The flowchart in FIG. 22 will be described below with reference to the arrangement in FIGS. 21A and 21B. In step S2201, the imaging apparatus 2101 obtains data by imaging the breasts of an object. The imaging apparatus 2101 uses a method of imaging the right and left breasts one by one. However, this apparatus may use a method of imaging both the breasts at once by using whole-body CT or MRI. In this case, the imaging apparatus 2101 can divide the obtained three-dimensional data of the right and left breasts into two parts.

In step S2202, the reconstructed image generation apparatus 2102 performs reconstruction processing based on the data obtained by the imaging apparatus 2101 to generate three-dimensional image data (reconstructed image data) of the breasts. The reconstructed image generation apparatus 2102 can also obtain data obtained in advance by imaging.

In step S2203, the storage apparatus 2103 stores the three-dimensional image data of the breasts generated by the reconstructed image generation apparatus 2102. In this case, the storage apparatus 2103 may store each three-dimensional image data in association with information indicating whether the data is about the right breast or left breast. In addition, the storage apparatus 2103 stores past tomographic images obtained by imaging and reconstruction in the past and image data obtained by other apparatuses such as a mammography apparatus.

In step S2204, the image processing apparatus 2104 performs image processing and image display as described later based on the three-dimensional image data of a plurality of breasts stored in the storage apparatus 2103. In addition, the image processing apparatus 2104 can display past three-dimensional image data, image data obtained by other imaging apparatuses such as a mammography apparatus, and the like stored in the storage apparatus 2103.

As described above, the image display system performs the processing in steps S2201 to S2204 to allow the operator to easily compare the reconstructed three-dimensional image data of a plurality of breasts. The image processing apparatus 2104 can also display tomographic image data obtained in the past and image data obtained by other imaging apparatuses. This enables the operator to browse more pieces of information at once.

Figure 23:
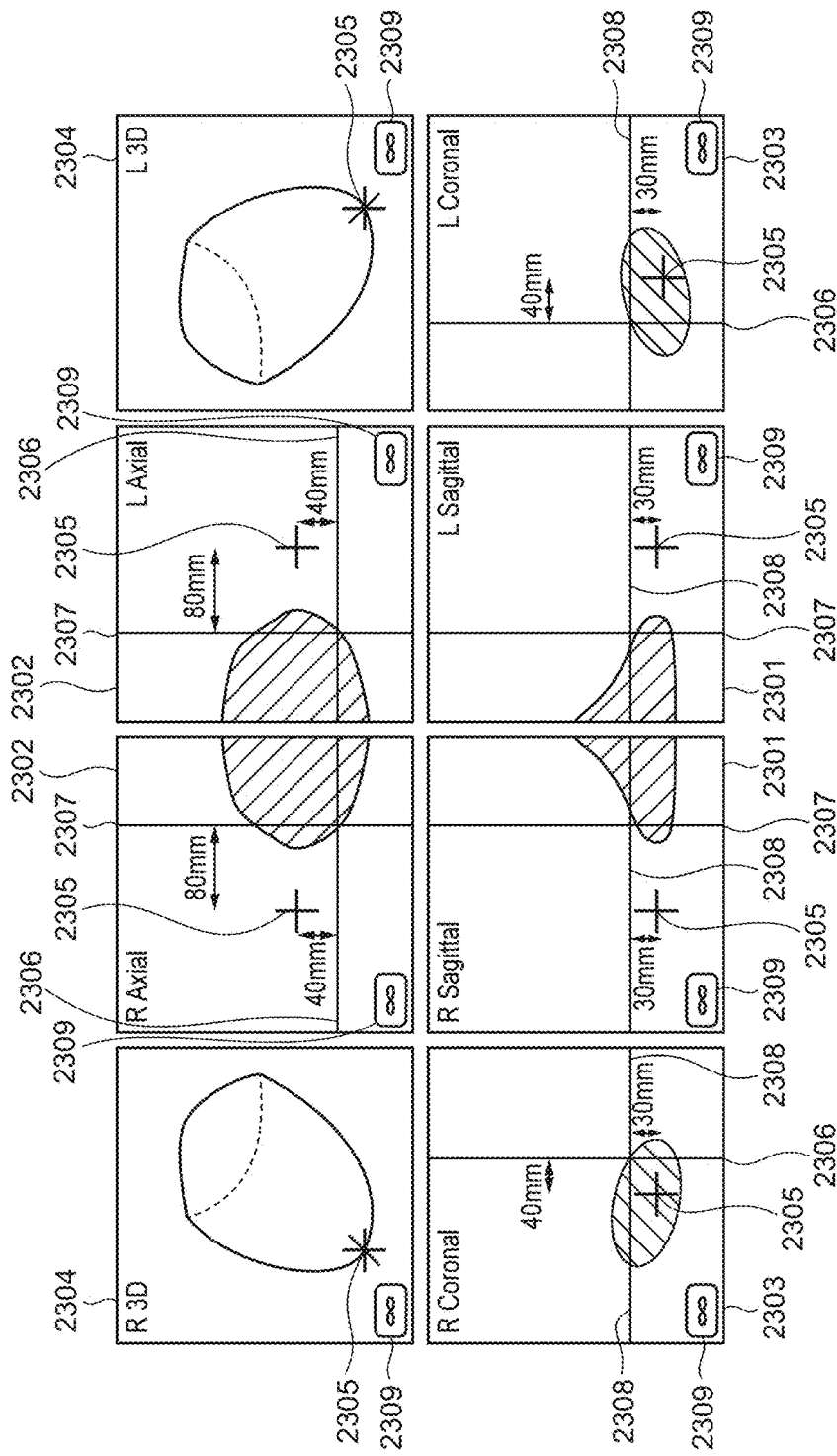
FIG. 23 is a schematic view showing an example of the display screen of the image processing apparatus 2104.

A method of comparatively displaying images of the right and left breasts in the image processing apparatus 2104 according to this embodiment will be described next. The arrangement of a screen displayed by the image processing apparatus 2104 will be described first with reference to FIG. 23. FIG. 23 is a schematic view showing an example of a display screen 2300 displayed by the image processing apparatus 2104 according to the embodiment.

In this embodiment, the display screen 2300 is segmented into eight segments, with images of the right breast being displayed on the left side of the middle of the screen, and images of the left breast being displayed on the right side. With regard to each breast, a sagittal display screen 2301, an axial display screen 2302, a coronal display screen 2303, and a volume display screen 2304 are displayed, which are display screens of tomographic images perpendicular to each other. An image obtained by volume rendering is displayed in the volume display screen 2304. Note that volume rendering is a method of constructing a three-dimensional image by using transparency information in addition to the luminance values of voxel data.

The positions of marks 2305 respectively indicated inside the sagittal display screens 2301, the axial display screens 2302, the coronal display screens 2303, and the volume display screens 2304 represent reference points for a plurality of three-dimensional image data of the breasts. The position of each reference mark 2305 indicates the coordinates of a papilla area in this embodiment. It is possible to decide the position of each reference mark 2305 by, for example, letting the operator select as well as by using a method using three-dimensional image data (to be described later).

Sagittal lines 2306 in the axial display screens 2302 and the coronal display screens 2303 each indicate the selected position of a tomographic image of a sagittal section. Coronal lines 2307 in the axial display screens 2302 and the sagittal display screens 2301 each indicate the selected position of a tomographic image of a coronal section. Axial lines 2308 in the coronal display screens 2303 and the sagittal display screens 2301 each indicate the selected position of a tomographic image of an axial section.

A link mark 2309 indicated inside each of the sagittal display screens 2301, the axial display screens 2302, the coronal display screens 2303, and the volume display screens 2304 is an index for deciding whether to change the other image in synchronism with a change in one of images of the right and left breasts. The operator can set the link mark 2309. When the link mark 2309 is set in a synchronization state, the other image is changed in synchronism with a change in one of the images. When the link mark 2309 is set in a non-synchronization state, the other image is not changed in synchronism with a change in one of the images. In this case, an operation on an image indicates a change in section position, enlargement/reduction, selection of a region of interest, adjustment of luminance/contrast, a change in slice thickness, or the like.

A method of displaying/selecting a sagittal section will be described next with reference to FIGS. 21B and 24. FIG. 21B is a block diagram showing the arrangement of the image processing apparatus 2104. In this embodiment, the image processing apparatus 2104 includes an obtaining unit 2111, a discrimination unit 2112, a reference setting unit 2113, an alignment unit 2114, a display control unit 2115, a selection unit 2116, a line position designation unit 2117, a line position setting unit 2118, and a generator 2119. Note that each functional block shown in FIG. 21B is implemented by hardware or software. When each functional block is implemented by software, a computer program for implementing each function is stored in a storage unit (not shown), and a CPU (Central Processing Unit) (not shown) executes the program, thereby implementing the function.

Figure 24:
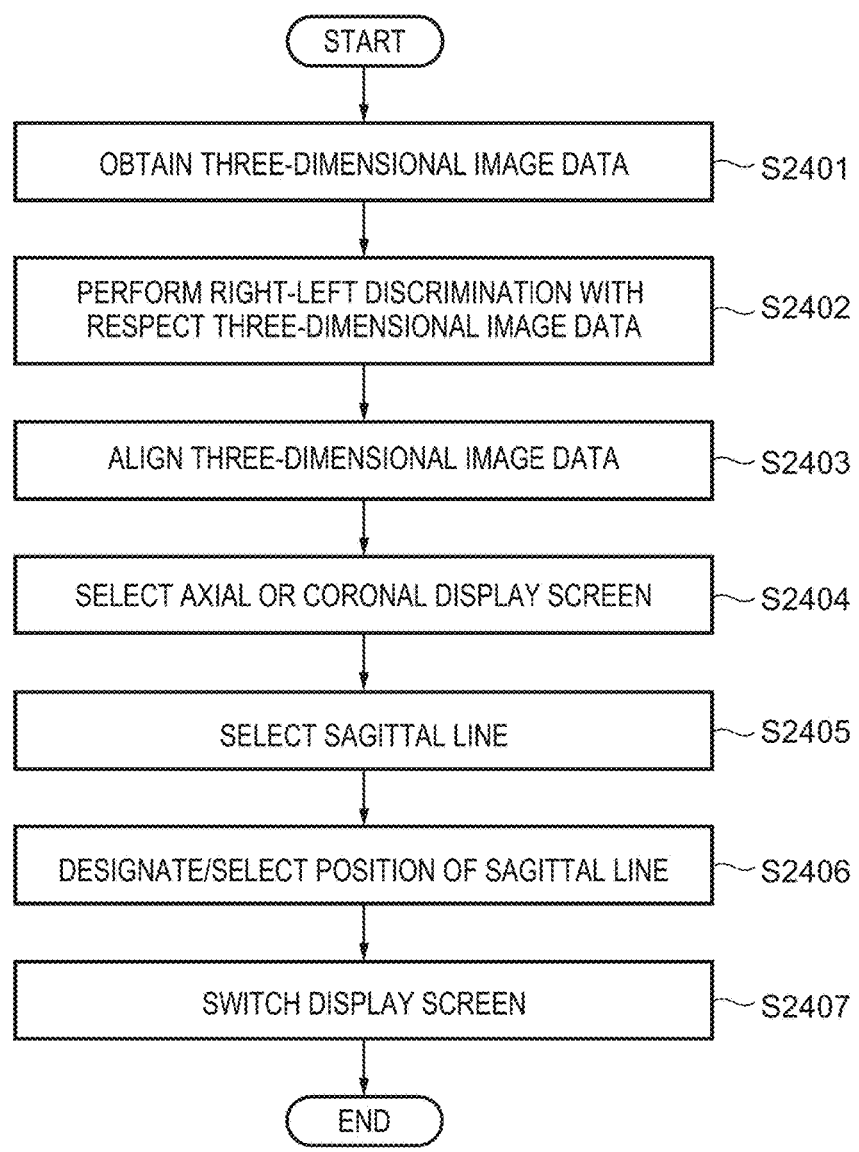
FIG. 24 is a flowchart showing processing by the image processing apparatus 2104.

FIG. 24 is a flowchart showing sagittal section display/selection processing by the image processing apparatus 2104. Assume that each link mark 2309 is set in a synchronization state unless otherwise specified.

In step S2401, the obtaining unit 2111 of the image processing apparatus 2104 obtains a plurality of three-dimensional image data stored in the storage apparatus 2103. In this embodiment, an object is the breast, and the obtaining unit 2111 obtains three-dimensional image data of the right and left breasts as the first and second three-dimensional image data. In step S2402, the discrimination unit 2112 of the image processing apparatus 2104 performs right-left discrimination concerning the first and second three-dimensional image data (the three-dimensional image data of the right and left breasts) obtained by the obtaining unit 2111. The discrimination unit 2112 can perform discrimination by using information or the like associated with image data. The discrimination unit 2112 can perform comparison with past images and comparison with images of other objects as well as left-right comparison.

In step S2403, the reference setting unit 2113 of the image processing apparatus 2104 sets reference points (the reference marks 2305 in FIG. 23) with respect to the first and second three-dimensional image data. In addition, the alignment unit 2114 adjusts the positions and tilts of the first and second three-dimensional image data (the three-dimensional data of the right and left breasts) and sets tomographic images of initial sagittal sections, axial sections, and coronal sections. The details of processing by the reference setting unit 2113 and the alignment unit 2114 will be described later. Note that the operator can change the coordinates of a papilla area and the tilt of an axis by operating an operation unit (not shown) while seeing the screen displayed by the image processing apparatus 2104. Upon setting the tomographic images of the initial sagittal sections, axial sections, and coronal sections, the reference setting unit 2113 sets reference points (reference marks 2305) in the tomographic images. As described above, in this embodiment, the position of the initial reference mark 2305 is the position of the papilla. Assume that in the embodiment, a sagittal section and an axial section are sections passing through a perpendicular line extending downward from the coordinates of a papilla area in the chest wall direction, and a coronal section is a section passing through a line perpendicular to a perpendicular line extending downward from the coordinates of a papilla area in the chest wall direction. That is, a sagittal section, an axial section, and a coronal section are perpendicular to each other.

The generator 2119 generates the first tomographic image with reference to a reference point from the first three-dimensional image data, and also generates the second tomographic image with reference to a reference point from the second three-dimensional image data in correspondence with the section of the first tomographic image. The display control unit 2115 causes a display unit (not shown) to symmetrically display the first and second tomographic images generated by the generator 2119. In this embodiment, the display control unit 2115 causes the display unit to display tomographic images of a sagittal section, axial section, and coronal section, which are a plurality of tomographic images with different section directions based on three-dimensional data whose positions and tilts have been adjusted by the alignment unit 2114.

In step S2404, the selection unit 2116 selects one of a plurality of tomographic images based on an input from the operator. More specifically, in order to decide a sagittal section, based on an input from the operator, the selection unit 2116 selects the axial display screen 2302 or the coronal display screen 2303 of one of right and left breast images. This sets the axial display screen 2302 or the coronal display screen 2303 in an active state. The display screen in an active state allows settings to be made.

In step S2405, the selection unit 2116 selects the sagittal line 2306 in the axial display screen 2302 or the coronal display screen 2303 selected in step S2404 based on an input from the operator. Selecting the sagittal line 2306 in this manner makes it possible to designate the position of the sagittal line 2306 in step S2406.

In step S2406, the line position designation unit 2117 designates the position of a line for specifying a section in a direction different from the section direction of the tomographic image selected in step S2404 based on an input from the operator. More specifically, the line position designation unit 2117 designates the position of the sagittal line 2306 in the axial display screen 2302 or the coronal display screen 2303 selected in step S2404 based on an input from the operator. Designating the position of the sagittal line 2306 in this manner makes it possible to select the position of a sagittal section. That is, a tomographic image of a sagittal section displayed in the sagittal display screen 2301 is decided.

In this case, since each link mark 2309 is set in a synchronization state, the line position setting unit 2118 sets the position of a line corresponding to the position of the line designated by the line position designation unit 2117 in one of a plurality of displayed tomographic images which has not been selected by the selection unit 2116. That is, the line position setting unit 2118 sets the positions of the sagittal lines 2306 on the right and left breasts so as to synchronously move them.

Such synchronous display will be described below. This embodiment is featured to display tomographic images with reference to the coordinates of the papilla areas (the reference marks 2305) of the right and left breasts as reference points so as to make the selected positions of the sagittal sections symmetrical to each other. When the line position designation unit 2117 designates the position of a line for specifying a tomographic image in the third direction in tomographic images in the first and second directions of three tomographic images perpendicular to each other in the three-dimensional image data of one breast, the line position setting unit 2118 sets the position of a line in a tomographic image which has not been selected by the selection unit 2116 so as to be symmetrical with the position of a line designated with reference to a reference point. That is, the line position designation unit 2117 designates the position of a line for specifying a section in another direction with reference to the reference point (the reference mark 2305). The line position setting unit 2118 then sets the position of a line in a tomographic image which has not been selected by the selection unit 2116 so as to be symmetrical with the position of the line designated with reference to the reference point.

For example, as shown in FIG. 23, the line position designation unit 2117 selects, as the position of the sagittal line 2306, a position shifted leftward from the coordinates of the papilla area by a distance of 40 mm in the coronal display screen 2303 of the right breast based on an input from the operator. In this case, the line position setting unit 2118 sets the sagittal line 2306 to a position shifted rightward from the coordinates of the papilla area by a distance of 40 mm in the coronal display screen 2303 of the left breast. In this manner, when each link mark 2309 is set in a synchronization state, displaying selected sagittal sections symmetrically allows the operator to accurately perform comparative observation of the three-dimensional image data of the right and left breasts.

Note that in this embodiment, the line position designation unit 2117 designates the position of the sagittal line 2306 based on an input from the operator. However, the position of the sagittal line 2306 may be designated by another method. For example, the selection unit 2116 may select the sagittal display screen 2301, and the line position designation unit 2117 may designate the position of the sagittal line 2306 based on a mouse wheel operation, the input of numerical values representing a section position, or the like.

In step S2407, the generator 2119 generates tomographic images of sections corresponding to the position of the line designated by the line position designation unit 2117 and the position of the line set by the line position setting unit 2118. The display control unit 2115 causes the display unit to symmetrically display the tomographic images generated by the generator 2119. More specifically, the display control unit 2115 causes the display unit to display the tomographic images upon switching sagittal sections in the sagittal display screens 2301 in accordance with the selected position of the sagittal line 2306. As described above, the image processing apparatus 2104 can switch the sagittal display screens 2301 by performing processing in steps S2401 to S2407.

Procedures for operations/processing in methods of displaying/selecting axial sections in the axial display screens 2302 are the same as those in the above methods of displaying/selecting sagittal sections. When selecting (switching) right and left axial sections, the line position designation unit 2117 designates the position of the axial line 2308 in the sagittal display screen 2301 or the coronal display screen 2303.

A method of displaying volume data will be described next. The display control unit 2115 changes the position/angle of an image itself in the volume display screen 2304 based on an input from the operator. In this case, the display control unit 2115 performs control to display tomographic images at angles respectively reverse to the angles in the sagittal and coronal directions in the screens of the right and left breasts with reference to the respective reference points (reference marks 2305). In addition, the display control unit 2115 performs control to display images of the right and left breasts, in the screens of the right and left breasts, at the same angles in the axial direction with reference to the reference marks 2305.

In addition, the display control unit 2115 performs control to display images of the right and left breasts at positions respectively reverse to the positions in the sagittal direction with reference to the respective reference marks 2305. The display control unit 2115 also performs control to display images of the right and left breasts at the same positions in the axial and coronal directions with reference to the respective reference marks 2305.

In this embodiment, the positions of the axial lines 2308 in the screens of the right and left breasts are displayed by selecting the same distance with reference to the coordinates of the respective papilla areas as reference points. For example, as shown in FIG. 23, the line position designation unit 2117 designates the axial section of the left breast image (axial line 2308) at a position shifted upward from the coordinates of the papilla area of the left breast by a distance of 30 mm. In this case, the line position setting unit 2118 also sets an axial section (axial line 2308) of the right breast image at a position shifted upward from the coordinates of the papilla area of the right breast by a distance of 30 mm. Displaying the tomographic images of axial sections at the same positions laterally allows the operator to accurately perform comparative observation of the three-dimensional image data of the right and left breasts.

The above sagittal section display method and an outline of operations/processing are the same as those when operating coronal sections. When selecting (switching) right and left coronal sections, the line position designation unit 2117 changes the positions of the coronal lines 2307 based on an input from the operator. In this case, as in the case of the above sagittal section display method, the coronal lines 2307 for the right and left breasts are set and displayed such that their positions are synchronously switched.

In this embodiment, the selected positions of the coronal lines 2307 with respect to the right and left breasts are selected at the same distance with reference to the coordinates of the respective papilla areas as reference points. For example, as shown in FIG. 23, the line position designation unit 2117 designates a coronal section (coronal line 2307) of a left breast image at a position shifted from the coordinates of the papilla area of the left breast toward the chest wall side by a distance of 80 mm. In this case, the line position setting unit 2118 automatically selects, as the position of a coronal section (coronal line 2307) of a right breast image, a position shifted from the coordinates of the papilla area of the right breast toward the chest wall side by a distance of 80 mm. When selecting coronal sections in this manner, they are set at the same positions in the lateral direction. Displaying tomographic images of coronal sections at laterally the same positions in this manner allows the operator to accurately perform comparative comparison between three-dimensional image data of the right and left breasts.

The following is a general description of the operations of the line position designation unit 2117 and the line position setting unit 2118 according to this embodiment. That is, when the line position designation unit 2117 designates the position of a line for specifying an axial section of a tomographic image of a coronal section or sagittal section of the three-dimensional image data of one breast, the line position setting unit 2118 sets the position of a line in a tomographic image of a coronal section or axial section of the three-dimensional image data of the other breast in the same direction at the same distance as those of the designated position of the line with reference a reference point.

In addition, when the line position setting unit 2118 designates the position of a line for specifying a sagittal section of a tomographic image of an axial section or coronal section of the three-dimensional image data of one breast, the line position setting unit 2118 sets the position of a line in a tomographic image of an axial section or coronal section of the three-dimensional image data of the other breast in the opposite direction by the same distance relative to the designated position of the line.

In addition, when the line position designation unit 2117 designates the position of a line for specifying a coronal section of a tomographic image of a sagittal section or axial section of the three-dimensional image data of one breast, the line position setting unit 2118 sets the position of a line in a tomographic image of a sagittal section or axial section of the three-dimensional image data of the other breast in the same direction at the same distance as those of the designated position of the line with reference to a reference point.

Alignment processing for the positions of the three-dimensional image data of the right and left breasts, which is the processing in step S2403 in FIG. 24, will be described next. FIG. 25 is a flowchart showing alignment processing by the reference setting unit 2113 and the alignment unit 2114 of the image processing apparatus 2104.

First of all, in step S2501, the reference setting unit 2113 specifies an object area including the breasts by performing binarization processing for the first and second three-dimensional image data (the three-dimensional image data of the right and left breasts) based on a threshold. In this case, the reference setting unit 2113 can use a predetermined threshold, a threshold obtained from an imaging condition and the size of the breast of the object, or the like as a threshold for binarization.

In step S2502, the reference setting unit 2113 searches for the position of the distal end of the binarized area. In this case, the distal end position indicates a position nearest to the papilla side in the chest wall-papilla direction. FIG. 26 is a schematic view showing three-dimensional breast image data. In this embodiment, slice numbers are assigned in ascending order from the chest wall side. The reference setting unit 2113 regards, as the distal end position, a slice position farthest from the chest wall side when seen from the papilla side, at which an area of the object exists, and sets the distal end position as the depth coordinates of the papilla. In the case shown in FIG. 26, a slice position at which the papilla exists is the position of the slice with the number "2606".

In step S2503, the reference setting unit 2113 obtains the barycentric position of two-dimensional image data at a slice position corresponding to the distal end position found in step S2502, and sets the obtaining position and the slice position described above as the coordinates of the papilla area, that is, the coordinates of the reference mark 2305. Note that the papilla area obtained in this manner is an approximate papilla area and indicates an area near the papilla. In addition, in the case of an object without any papilla, the reference setting unit 2113 sets coordinates set in this step as the coordinates of a papilla area.

In step S2504, the alignment unit 2114 translates the three-dimensional image data of the right and left breasts. More specifically, the alignment unit 2114 translates the three-dimensional image data so as to arrange the coordinates of the right and left papilla areas at predetermined coordinates. The alignment unit 2114 uses rigid-body transformation or affine transformation for translation.

In step S2505, the alignment unit 2114 adjusts the tilts of the three-dimensional image data of the right and left breasts. In this embodiment, the alignment unit 2114 matches the tilts of the three-dimensional image data of the right and left breasts by changing the tilt of the three-dimensional image data of the left breast with reference to the three-dimensional image data of the right breast.

FIGS. 27A and 27B are views showing an example of adjusting the three-dimensional image data of the right and left breasts in step S2505. FIG. 27A shows the three-dimensional image data of the right breast. FIG. 27B shows the three-dimensional image data of the left breast. In this embodiment, reference image data is image data obtained by laterally inverting the three-dimensional image data of the right breast with reference to a perpendicular line 2701 extending downward from the papilla to the chest wall side. The alignment unit 2114 rotates the three-dimensional image data of the left breast to make it near the three-dimensional image data of the right breast, with coordinates 2702 of the papilla area of the three-dimensional image data of the left breast in FIG. 27B being an origin. The alignment unit 2114 performs this rotation by rigid-body transformation, affine transformation, or the like. Note that a rotational angle is obtained by using a known point correspondence method, surface shape collation method, or the like. The alignment unit 2114 rotates the three-dimensional image data of the left breast through the obtained rotational angle.

In this manner, the reference setting unit 2113 and the alignment unit 2114 perform the processing in steps S2501 to S2505 to adjust the coordinates of the papilla areas and the tilts of the breasts. If the difference between the volumes obtained from the image data of the two breasts by the alignment unit 2114 after processing in step S2501 exceeds a threshold, alignment processing in steps S2502 to S2505 can be omitted. This makes it possible to cope with an object whose right and left breasts considerably differ in shape.

In addition, placing a limitation on a rotational angle for rotation processing in step S2505 is effective in preventing the rotational angle from becoming considerably large. This reduces the search range of rotational angles and hence makes it possible to expect an increase in processing speed. In addition, in this embodiment, in order to match the tilts of the image data of the right and left breasts, the alignment unit 2114 compares the three-dimensional image data themselves. However, the alignment unit 2114 may compare data obtained by reducing the three-dimensional image data. This makes it possible to expect simplification of processing and an increase in processing speed. Note that the alignment unit 2114 may convert the reduced data into binary data.

In addition, in this embodiment, the alignment unit 2114 corrects the tilts after translating the coordinates of the papilla areas to predetermined areas. However, for example, the alignment unit 2114 may simultaneously perform translation and rotation with respect to the three-dimensional image data of the left breast so as to make the data nearest to the reference image (the three-dimensional image data of the right breast). In this case, the reference setting unit 2113 may use, for example, a method of setting the barycenter of a plurality of three-dimensional image data as a reference point, instead of setting a papilla area as a reference point. In addition, the alignment unit 2114 may use, for example, a method of correcting tilts by estimating chest wall planes from image data as well as from the coordinates of papilla areas, and matching the angles of perpendicular lines extending downward from the papilla areas to the chest wall planes. In this case, the reference setting unit 2113 can use, for example, a method of setting, as a reference point, a midpoint of a reference axis instead of a papilla area.

As described above, the image processing apparatus according to this embodiment aligns images of the right and left breasts first, and then selects a position corresponding to (synchronizing with) a position designated in one of the images from the other image with reference to a predetermined position, thereby performing display. This allows the operator to accurately perform comparative observation of the three-dimensional image data of the right and left breasts.

[Modification]

Although the fourth embodiment is targeted to the three-dimensional image data of different objects, the embodiment may be targeted to a plurality of three-dimensional image data obtained by imaging the same object at different times in the same direction. That is, the embodiment configured to perform display for comparison between the different right and left breasts can also be applied to comparison between image data obtained at different times in the same direction or breast images of other objects. In this case, the alignment unit 2114 may perform alignment without performing lateral inversion processing. In addition, in this case, the line position setting unit 2118 can set a line in the same direction at the same distance relative to the position of a line designated by the line position designation unit 2117. For example, in the above case, the line position setting unit 2118 can set line positions in the axial direction, the coronal direction, and the sagittal direction in the same direction at the same distance relative to the coordinates of a papilla area as a reference point. This allows the operator to compare also image data obtained in the past.

Fifth Embodiment

The fifth embodiment will exemplify a display method for oblique sections. Differences from the fourth embodiment will be described below.

Figure 28:
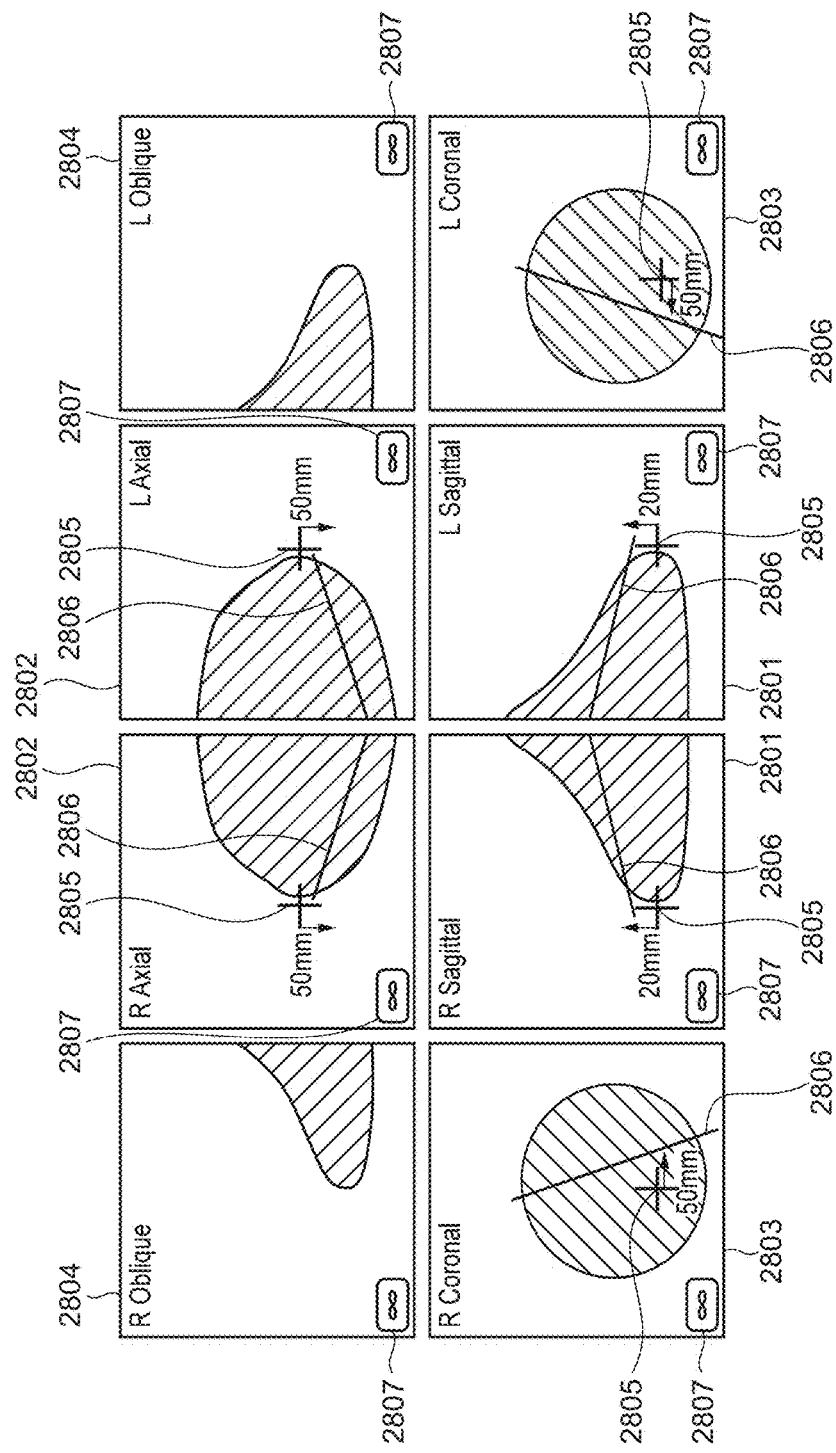
FIG. 28 is a schematic view showing an example of the display screen of a display apparatus 2800.

FIG. 28 is a view showing an example of a display screen 2800 of an image processing apparatus 2104 according to this embodiment. In this embodiment, the display screen 2800 is segmented into eight segments, with the right breast being displayed on the left side of the middle of the screen, and the left breast being displayed on the right side. With regard to the respective breasts, the following screens are displayed: sagittal display screens 2801 for displaying tomographic images perpendicular to each other, axial display screens 2802, coronal display screens 2803, and oblique display screens 2804 for displaying tomographic images in a direction other than the directions of the three other sections. In the oblique display screens 2804, tomographic images of arbitrarily tilted oblique sections are displayed.

The positions of reference marks 2805 respectively indicated in the sagittal display screens 2801, the axial display screens 2802, and the coronal display screens 2803 indicate the reference points of the three-dimensional data of the right and left breasts. In this embodiment, the positions of the reference marks 2805 indicate the coordinates of papilla areas in the right and left three-dimensional image data. It is possible to use the same method as that in the fourth embodiment as a method of deciding reference points.

Oblique lines 2806 in the sagittal display screens 2801, the axial display screens 2802, and the coronal display screens 2803 respectively indicate the selected positions of oblique sections. In addition, a link mark 2807 in each display screen indicates whether when one of the images of the right and left breasts is operated, the other image also synchronously changes. The operator can set the link mark 2309. When the link mark 2309 is set in a synchronization state, the other image is changed in synchronism with a change in one image. When the link mark 2309 is set in a non-synchronization state, the other image is not changed in synchronism with a change in one image. In this case, an operation on an image indicates a change in section position, enlargement/reduction, selection of a region of interest, adjustment of luminance/contrast, a change in slice thickness, or the like.

Figure 29:
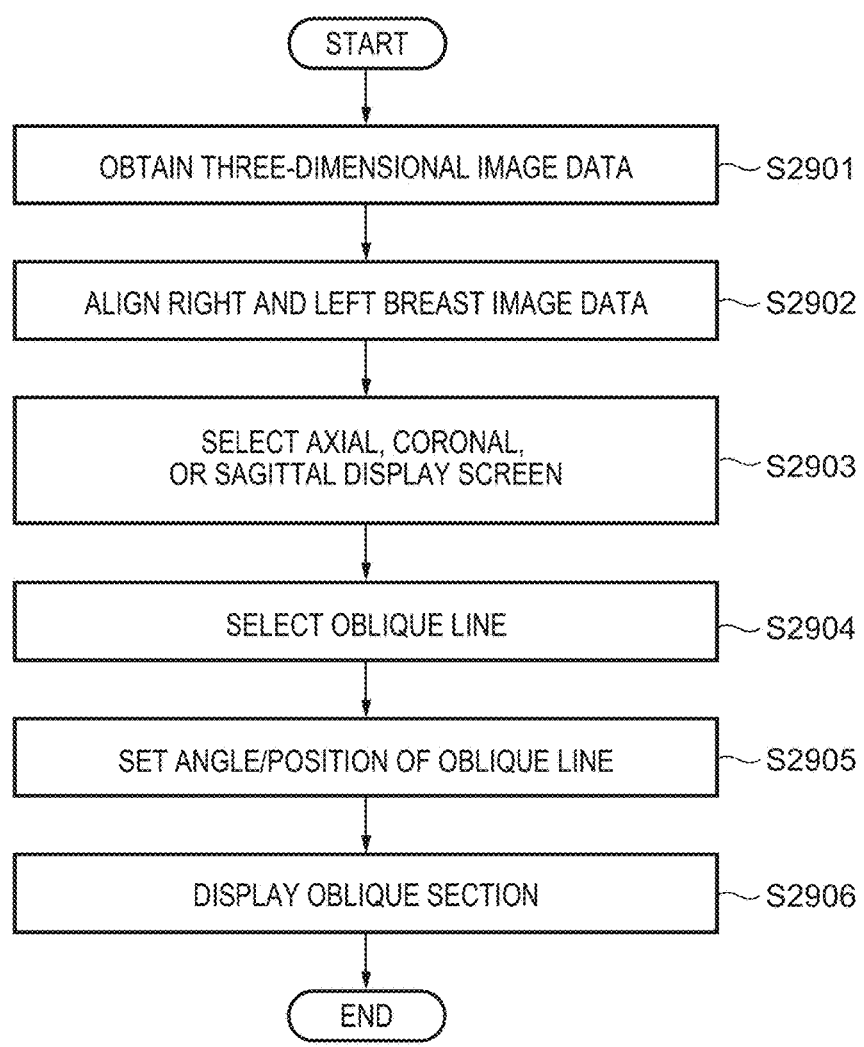
FIG. 29 is a flowchart showing an operation using the image processing apparatus 2104.

A method of displaying/selecting an oblique section will be described next with reference to FIG. 29. FIG. 29 is a flowchart showing a procedure for oblique section display/selection processing by the image processing apparatus 2104. Assume that each link mark 2807 is set in a synchronization state unless otherwise specified.

In step S2901, an obtaining unit 2111 of the image processing apparatus 2104 obtains the first and second three-dimensional image data (the three-dimensional image data of the right and left breasts) stored in the storage apparatus 2103. In step S2902, the reference setting unit 2113 of the image processing apparatus 2104 sets a reference point (the reference mark 2805 in FIG. 28). An alignment unit 2114 aligns the three-dimensional image data of the right and left breasts, and sets initial sagittal sections, axial sections, coronal sections, and oblique sections. It is possible to use the same method as that in the fourth embodiment as a method of deciding reference points. Assume that in this embodiment, the initial position of an oblique section is the same as that of a sagittal section. Note that the operator can change the coordinates of a papilla area and the tilt of an axis by operating an operation unit (not shown) while seeing a screen displayed on the image processing apparatus 2104.

In step S2903, a selection unit 2116 selects one of a plurality of tomographic images based on an input from the operator. More specifically, in order to decide an oblique section, the selection unit 2116 selects one of the sagittal display screen 2801, the axial display screen 2802, and the coronal display screen 2803 of one the right and left breasts. This sets one of the sagittal display screen 2801, the axial display screen 2802, and the coronal display screen 2803 in an active state. Settings can be made on the display screen in the active state.

In step S2904, the selection unit 2116 selects the oblique line 2806 in the screen selected in step S2903 based on an input from the operator. Selecting the oblique line 2806 in this manner will set a state in which the position of the oblique line 2806 can be designated in step S2905.

In step S2905, a line position designation unit 2117 designates the position and angle of a line for specifying a section in a direction different from that of the section of the tomographic image selected in step S2903 based on an input from the operator. More specifically, the line position designation unit 2117 designates the position and angle of the oblique line 2806 in the screen selected in step S2903 based on an input from the operator. Designating the position and angle of the oblique line 2806 in this manner will set a state in which the position of an oblique section can be selected. That is, a tomographic image of an oblique section is decided.

Note that in this embodiment, in step S2905, the line position designation unit 2117 designates the position of the oblique line 2806 based on an input from the operator. However, the line position designation unit 2117 may designate the position by using another method. For example, the selection unit 2116 may select a display screen for each section, and the line position designation unit 2117 may set the position of the oblique line 2806 based on a mouse wheel operation, the input of numerical values representing a section position, or the like. In addition, since the link mark 2807 is set in a synchronization state, a line position setting unit 2118 sets the position and angle of the line to synchronously move the positions of the oblique lines 2806 on the right and left breasts. A method of designating the angle and position of the oblique line 2806 will be described in detail later.

In step S2906, a generator 2119 generates tomographic images of sections in oblique directions corresponding to the positions and angles of the lines designated by the line position designation unit 2117 and the positions and angles of the lines set by the line position setting unit 2118. A display control unit 2115 causes the display unit to symmetrically display the tomographic images generated by the generator 2119. More specifically, the display control unit 2115 displays the tomographic images of the oblique sections in the oblique display screens in accordance with the selected positions and angles. The image processing apparatus 2104 performs operations/processing in steps S2901 to S2906 in this manner to allow the operator to easily perform comparative interpretation on the oblique sections.

Figure 30:
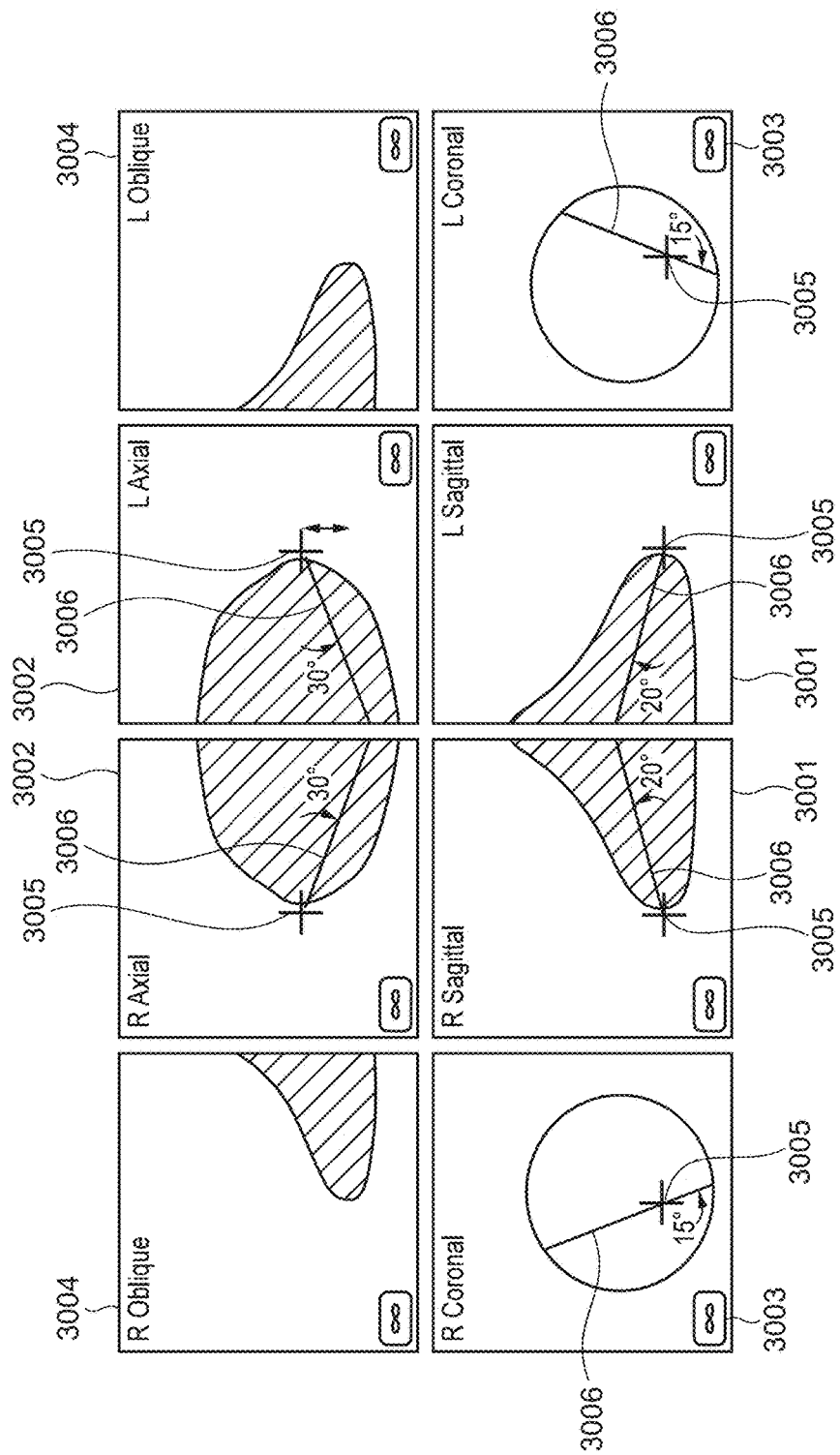
FIG. 30 is a schematic view showing an example of setting the angle of an oblique section using the display apparatus 2800.

A method of designating the angle and position of the oblique line 2806 will be described next. In this embodiment, the angle of the oblique line 2806 is designated based on the position of the papilla as a reference point. FIG. 30 is a view showing an example of setting the angle of the oblique line 2806. Referring to FIG. 30, the position of a reference mark 3005 indicates a reference point, and indicates a papilla area in this embodiment. The operator can set the angles of oblique lines 3006 in sagittal display screens 3001, axial display screens 3002, and coronal display screens 3003.

Figure 31:
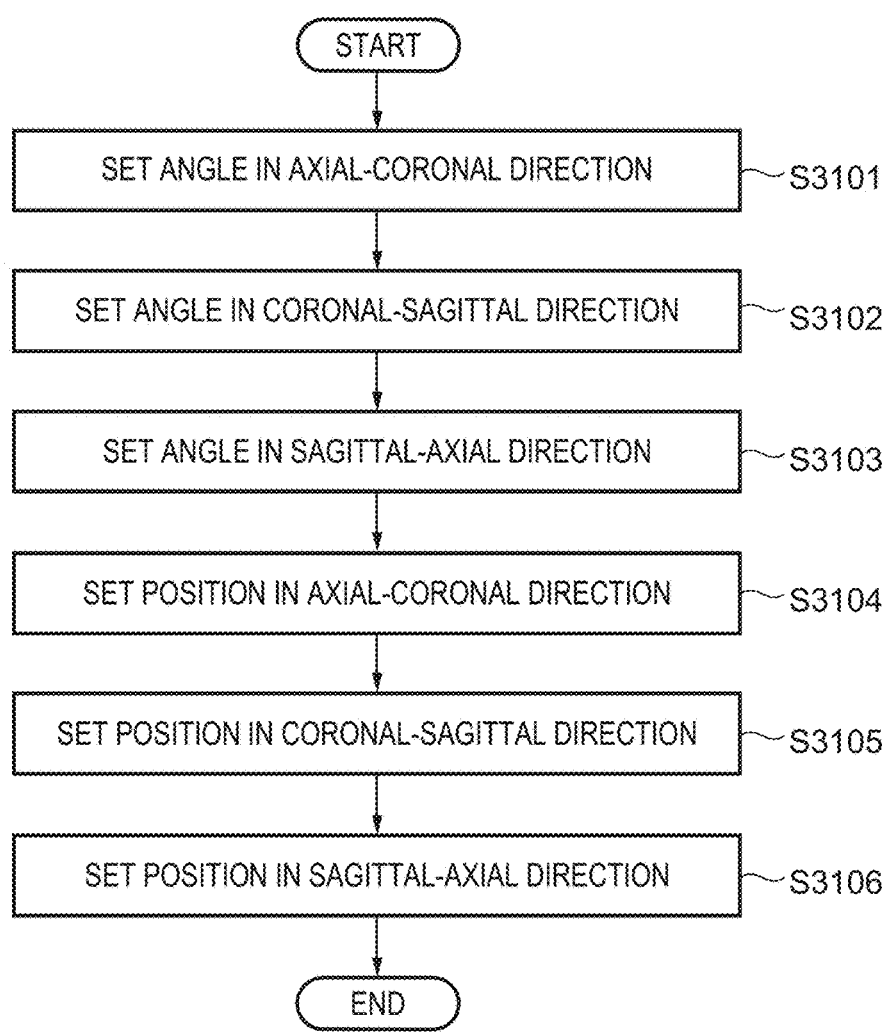
FIG. 31 is a flowchart showing an operation when setting the angle and position of an oblique section using the display apparatus 2800.

FIG. 31 is a flowchart showing an example of angle/position setting processing for the oblique line 3006. In this embodiment, when the line position designation unit 2117 designates the position of a line for specifying a tomographic image in the third direction in tomographic images in the first and second directions of three tomographic images perpendicular to each other in the three-dimensional image data of one breast, the line position setting unit 2118 sets the position of a line in a tomographic image which has not been selected by the selection unit 2116 so as to be symmetrical with the position of the line designated with reference to the reference point.

First of all, in step S3101, the line position designation unit 2117 designates an angle in an axial-coronal direction in the sagittal display screen 3001 based on an input from the operator. The operator inputs an angle with respect to one of the oblique lines 3006 in the sagittal display screens 3001 of the three-dimensional image data of the right and left breasts. In accordance with this operation, the line position designation unit 2117 designates an angle. Since each link mark 3003 is set in a synchronization state, the line position setting unit 2118 sets the oblique line 3006 in one of the images of the right and left breasts which has not been operated by the operator. When, for example, as shown in FIG. 30, the oblique line 3006 is designated at 20° toward the head side with reference to the coordinates of the papilla area as an origin in the left tomographic image, the line position setting unit 2118 sets the oblique line 3006 at 20° toward the head side with reference to the coordinates of the papilla area as an origin in the right tomographic image.

In step S3102, the line position designation unit 2117 designates an angle in the coronal-sagittal direction in the axial display screen 3002 based on an input from the operator. The operator inputs an angle with respect to one of the oblique lines 3006 in the axial display screens 3002 of the three-dimensional image data of the right and left breasts. In accordance with this operation, the line position designation unit 2117 designates an angle. Since each link mark 3003 is set in a synchronization state, the line position setting unit 2118 sets the oblique line 3006 in one of the images of the right and left breasts which has not been operated by the operator. When, for example, as shown in FIG. 30, the oblique line 3006 is designated at 30° counterclockwise with reference to the coordinates of the papilla area as an origin in the right image, the line position setting unit 2118 sets the oblique line 3006 at 30° clockwise with reference to the coordinates of the papilla area as an origin in the left image.

Subsequently, in step S3103, the line position designation unit 2117 designates an angle in the sagittal-axial direction in the coronal display screen 3003 based on an input from the operator. The operator inputs an angle with respect to one of the oblique lines 3006 in the coronal display screens 3003 of the three-dimensional image data of the right and left breasts. In accordance with this operation, the line position designation unit 2117 designates an angle. Since each link mark 3003 is set in a synchronization state, the line position setting unit 2118 sets the oblique line 3006 in one the images of the right and left breasts which has not been operated by the operator. When, for example, as shown in FIG. 30, the oblique line 3006 is designated at 15° counterclockwise with reference to the coordinates of the papilla area as an origin in the right image, the line position setting unit 2118 sets the oblique line 3006 at 15° clockwise with reference to the coordinates of the papilla area as an origin in the left image.

In step S3104, the line position designation unit 2117 designates the position of the oblique line 3006 in the axial-coronal direction in the sagittal display screen 3001 based on an input from the operator. The operator inputs the position of the oblique line 3006 in one of the sagittal display screens 3001 of the three-dimensional image data of the right and left breasts. In accordance with this operation, the line position designation unit 2117 designates the position of the oblique line 3006. Since each link mark 3003 is set in a synchronization state, the line position setting unit 2118 sets the oblique line 3006 in one of the images of the right and left breasts which has not been selected by the selection unit 2116.

More specifically, when the line position designation unit 2117 designates the position of the oblique line 3006 in one of images in the axial direction, the oblique line 3006 is set in the same direction as the designated position, with the reference mark 3005 being an origin. For example, as shown in FIG. 28, when the oblique line 2806 is designated at a position shifted from the coordinates of the papilla area as an origin toward the head side by 20 mm in the right image, the line position setting unit 2118 sets the oblique line 2806 to a position shifted from the coordinates of the papilla area as an origin toward the head side by 20 mm in the left image. In addition, it is possible to change the position of the oblique line 3006 in each sagittal display screen 3001 in the coronal direction. In this case as well, when the line position designation unit 2117 designates the position of the oblique line 3006 in one image in the axial direction, the oblique line 3006 in the other image is set in the same direction as that at the designated position, with the reference mark 3005 being an origin. When, for example, the oblique line 3006 is designated at a position shifted from the coordinates of the papilla area by 20 mm in the chest wall direction in the right image, the line position setting unit 2118 sets the oblique line 3006 in the left image at a position shifted from the coordinates of the papilla area by 20 mm in the chest wall direction.

In step S3105, the line position designation unit 2117 sets the oblique line 3006 at a position in the coronal-sagittal direction in the axial display screen 3002 based on an input from the operator. The operator inputs the position of the oblique line 3006 in one of the axial display screens 3002 of the three-dimensional image data of the right and left breasts. In accordance with this operation, the line position designation unit 2117 designates the position of the oblique line 3006. Since each link mark 3003 is set in a synchronization state, the line position setting unit 2118 sets the oblique line 3006 in one of the images of the right and left breasts which has not been selected by the selection unit 2116.

For example, as shown in FIG. 28, when the oblique line 2806 is set at a position shifted leftward from the coordinates of the papilla area by a distance of 50 mm in the right image, the line position setting unit 2118 sets the oblique line 2806 at a position shifted rightward from the coordinates of the papilla area by a distance of 50 mm in the left image. In the axial display screen 3002, like the sagittal display screen 3001, it is possible to change the position in the coronal direction. When the line position designation unit 2117 changes the position of the oblique line in the coronal direction, the line position setting unit 2118 sets the position of the oblique line in the same direction as that of the position designated by the operator, with the reference mark being an origin.

In step S3106, the line position designation unit 2117 sets the oblique line 3006 in the sagittal-axial direction in the coronal display screens 3003 based an input from the operator. The operator inputs the position of the oblique line 3006 in one of the coronal display screens 3003 of the three-dimensional image data of the right and left breasts. In accordance with this operation, the line position designation unit 2117 designates the position of the oblique line 3006. Since each link mark 3003 is set in the synchronization state, the line position setting unit 2118 sets the oblique line 3006 in one of the images of the right and left breasts which has not been selected by the selection unit 2116.

When, for example, as shown in FIG. 28, the oblique line 2806 is set at a position shifted leftward from the coordinates of the papilla area by a distance of 50 mm in the right image, the line position setting unit 2118 sets the oblique line 2806 at a position shifted rightward from the coordinates of the papilla area by a distance of 50 mm in the left image. Like the sagittal display screen 3001, the coronal display screen 3003 allows a change in the position of a line in the axial direction. When the line position designation unit 2117 changes the position of the line in the axial direction, the line position setting unit 2118 sets the line in the same direction as that of the position designated by the operator, with the reference mark 3005 being an origin.

The overall operation of the line position designation unit 2117 and the line position setting unit 2118 according to this embodiment will be described below. That is, when the line position designation unit 2117 designates the angle of a line for specifying an oblique section of a tomographic image of a coronal section or axial section of the three-dimensional image data of one of the breasts, the line position setting unit 2118 sets the angle of a line to the same angle as the designated angle of the line in the opposite direction in a tomographic image of a coronal section or axial section of the three-dimensional image data of the other breast, with a reference point being an origin.

In addition, when the line position designation unit 2117 designates the angle of a line for specifying an oblique section of a tomographic image of a sagittal section of the three-dimensional image data of one of the breasts, the line position setting unit 2118 sets the angle of a line to the same angle as the designated angle of the line in the same direction in a tomographic image of a sagittal section of the three-dimensional image data of the other breast, with a reference being an origin.

Furthermore, when the line position designation unit 2117 designates the position of a line for specifying an oblique section of a tomographic image of a sagittal section of the three-dimensional image data of one of the breasts, the line position setting unit 2118 sets the position of a line in the same direction at the same distance as those of the designated position of the line in a tomographic image of a sagittal section of the three-dimensional image data of the other breast, with a reference being an origin.

Moreover, when the line position designation unit 2117 designates the position of a line for specifying an oblique section of a tomographic image of an axial section or coronal section of the three-dimensional image data of one of the breasts, the line position setting unit 2118 sets the position of a line in the opposite direction at the same distance relative to the designated position of the line in a tomographic image of an axial section or coronal section of the three-dimensional image data of the other breast, with a reference being an origin.

As described above, the image processing apparatus 2104 can set the angles and positions of the oblique lines 2806 by performing the processing in steps S3101 to S3106. As described above, it is possible to facilitate comparative interpretation by symmetrically setting the angles of the oblique lines in the sagittal direction and the coronal direction with reference to the positions of the papillae as reference points and setting the angles of the oblique lines in the axial direction to the same angles with reference to the positions of the papillae. In addition, setting the papillae as references makes it easy to recognize the distribution of mammary gland tissue. In addition, the line position setting unit 2118 sets the positions of lines in the sagittal direction to symmetrical positions with respect to the coordinates of the respective papillae, the positions of lines in the axial direction to the same positions in the craniocaudal direction with respect to the coordinates of the respective papillae, and the positions of lines in the coronal direction to the same positions in the chest wall-papilla direction with respect to the coordinates of the papillae. This can facilitate comparative interpretation.

Note that in this embodiment, the operator performs angle setting and position setting with respect to the oblique lines 3006 in the order named, and also performs each setting operation in the axial-coronal direction, the coronal-sagittal direction, and the sagittal-axial direction in the order named. However, the orders of operations are not limited to them. In addition, the operator may perform some of these operations.

In addition, when the operator wants to change the angle of a line after changing its position, he/she can change the angle by shifting the reference point from the coordinates of the papilla area by a set value and changing the angle with the shifted reference point as an origin in each direction. Furthermore, when the operator wants to simultaneously designate the position and angle of a line, he/she can designate them by designating arbitrary two points on each section. In this case, as in the above case of oblique line setting, the other oblique line is set such that the positions of the right and left images become symmetrical. Moreover, if the position/angle setting of an oblique line influences oblique lines in sections other than the same section, position/angle setting is synchronously performed.

[Modification]

In the fifth embodiment, the position of an oblique section is designated to perform angle setting. However, it is possible to set an oblique section by matching the oblique angle with that of an image obtained by another imaging apparatus such as a mammography apparatus. In this case, the obtaining unit 2111 further obtains a plurality of three-dimensional image data obtained by an imaging apparatus different from the imaging apparatus for generating the plurality of three-dimensional image data described above at imaging angles corresponding to the angles of lines designated by the line position designation unit 2117.

Figure 32:
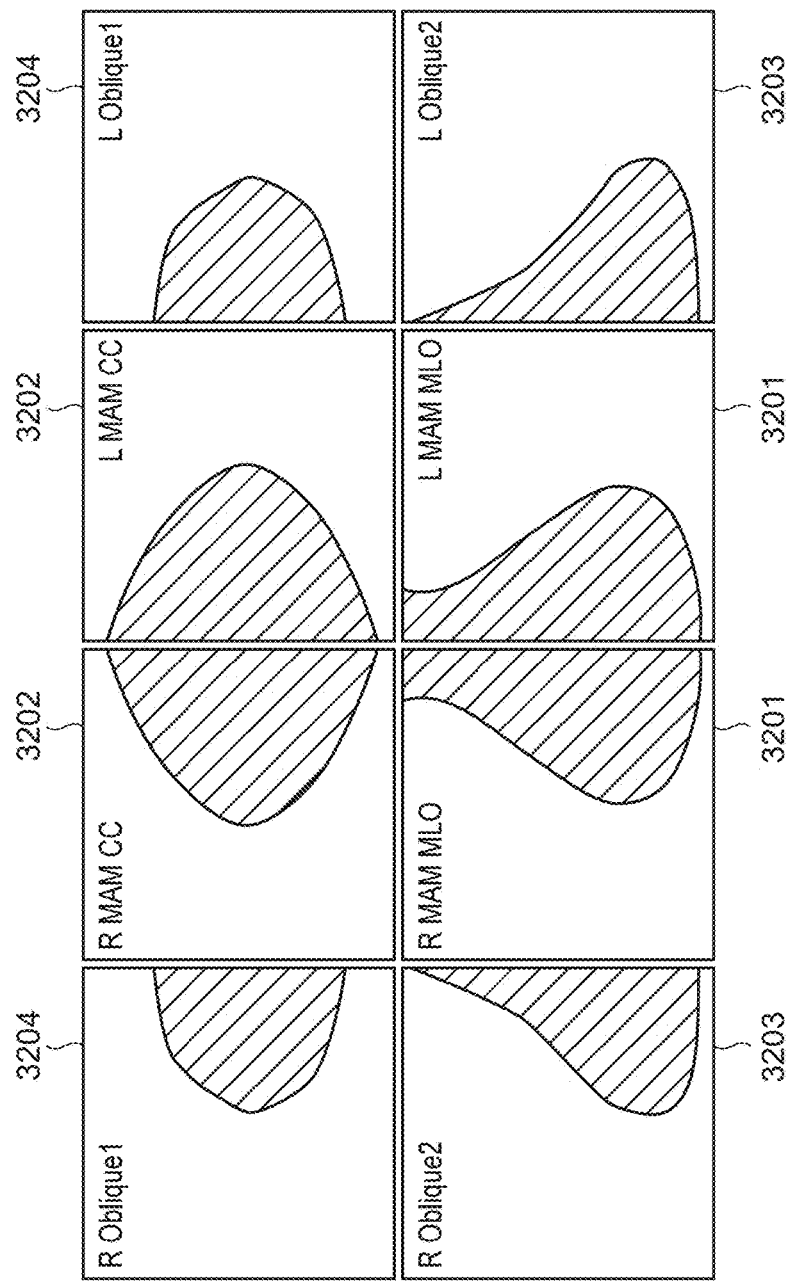
FIG. 32 is a schematic view showing an example of simultaneously displaying mammograms and three-dimensional image data of the breasts using the display apparatus 2800.

FIG. 32 is a view comparatively showing images obtained by mammography and oblique sections of three-dimensional image data. Screens 3201 are screens for displaying images obtained by MLO (Medio-Lateral Oblique) imaging using a mammography apparatus. Screens 3202 are screens for displaying images obtained by CC (craniocaudal) imaging using a mammography apparatus. Screens 3203 are screens for displaying tomographic images of oblique sections of the three-dimensional image data of the breasts. Screens 3204 are screens for displaying tomographic images of oblique sections of the three-dimensional image data of the breasts which are different from the screens 3203.

Assume that in this modification, MLO imaging is performed such that the apparatus is rotated through 65° counterclockwise to image the left breast, and is rotated through 65° clockwise to image the right breast. Assume also that CC imaging is performed to image both the right and left breasts without rotating the apparatus.

Oblique sections are set for the screens 3203 in accordance with MLO imaging. For this reason, the oblique section of the screen 3203 of the right breast is rotated through 65° from the initial sagittal section of the axial-sagittal section, and the oblique section of the left breast is rotated through 65° clockwise. In addition, the oblique sections in the screens 3203 are set in accordance with CC imaging. For this reason, the oblique sections in the screens 3204 are identical to the axial sections. Note that angle information at this time is provided in association with image data. Comparing images obtained by different imaging apparatuses with each other makes it possible to obtain more diagnosis information.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-168086, filed Aug. 27, 2015, and No. 2015-169728, filed Aug. 28, 2015, which are hereby incorporated by reference herein in their entirety.

What is claimed is:

1. An image processing apparatus comprising:
a memory storing a program; and
one or more processors which, by executing the program, function as units comprising:
(1) a right region image obtaining unit configured to obtain a three-dimensional radiation image of a right region of substantially symmetrical regions;
(2) a left region image obtaining unit configured to obtain a three-dimensional radiation image of a left region of the substantially symmetrical regions;
(3) an alignment unit configured to perform alignment between the three-dimensional radiation image of the right region and the three-dimensional radiation image of the left region based on a feature position of the regions;
(4) a display control unit configured to substantially symmetrically arrange and display the three-dimensional radiation image of the right region and the three-dimensional radiation image of the left region which have been aligned, and a tomographic image of the right region and a tomographic image of the left region; and
(5) an operation unit configured to change a section position of one of the tomographic image of the right region and the tomographic image of the left region,
wherein the display control unit (a) changes a section position of the other tomographic image of the tomographic image of the right region and the tomographic image of the left region in conjunction with a change in the section position of the one tomographic image by the operation unit, in a case that the alignment unit has performed alignment between the three-dimensional radiation image of the right region and the three-dimensional radiation image of the left region, and (b) substantially symmetrically arranges and displays (i) the tomographic image of the right region that corresponds to the changed section position of the tomographic image of the right region and (ii) the tomographic image of the left region that corresponds to the changed section position of the tomographic image of the left region.

2. The apparatus according to claim 1, further comprising a detection unit configured to detect, as the feature position, a three-dimensional feature position.

3. The apparatus according to claim 1, wherein the display control unit displays a plurality of radiation images of axial tomographic images, sagittal tomographic images, coronal tomographic images, and three-dimensional images of the right region and the left region in a first layout pattern in which the plurality of radiation images are arranged substantially symmetrically.

4. The apparatus according to claim 3, wherein the display control unit displays a plurality of radiation images of an axial tomographic image, a sagittal tomographic image, a coronal tomographic image, and a three-dimensional image of the right region and a plurality of radiation images of an axial tomographic image, a sagittal tomographic image, a coronal tomographic image, and a three-dimensional image of the left region in a second layout pattern in which the plurality of radiation images of the right region are arranged substantially symmetrically with respect to the plurality of radiation images of the left region.

5. The apparatus according to claim 4, wherein the display control unit switches between the first layout pattern and the second layout pattern.

6. The apparatus according to claim 1, wherein the operation unit moves one of the radiation images of the right region and the left region on a display screen, and
wherein the display control unit displays the other radiation image upon moving the image on the display screen in accordance with movement of the one radiation image.

7. The apparatus according to claim 1, further comprising a superimposing unit configured to superimpose a radiation image of a right region and the radiation image of the left region, which have been aligned, upon substantially symmetrically arranging the radiation images.

8. The apparatus according to claim 1, wherein the alignment unit performs alignment between the radiation image obtained at a first time and the radiation image obtained at a second time based on the feature position, and
wherein the display control unit arranges and displays the radiation images obtained at the first time and the second time, which have been aligned, substantially symmetrically.

9. The apparatus according to claim 1, wherein each of the left region and the right region comprises a breast,
wherein the right region image obtaining unit obtains the three-dimensional radiation image of a right breast,
wherein the left region image obtaining unit obtains the three-dimensional radiation image of a left breast,
wherein the alignment unit performs alignment between the three-dimensional radiation image of the right breast and the three-dimensional radiation image of the left breast based on the feature position, and
wherein the display control unit arranges and displays the three-dimensional radiation image of the right breast and the three-dimensional radiation image of the left breast, which have been aligned, substantially symmetrically.

10. A radiation imaging system comprising:
a memory storing a program; and
one or more processors which, by executing the program, function as units comprising:
(1) a first imaging unit configured to obtain a radiation image while rotating around a breast arranged from a first direction;
(2) a second imaging unit configured to obtain a radiation image of a breast compressed or arranged from a second direction different from the first direction;
(3) a right region image obtaining unit configured to obtain a three-dimensional radiation image of a right breast imaged by the first imaging unit;
(4) a left region image obtaining unit configured to obtain a three-dimensional radiation image of a left breast imaged by the first imaging unit;
(5) an alignment unit configured to perform alignment between the three-dimensional radiation image of the right breast and the three-dimensional radiation image of the left breast based on a feature position of the regions;
(6) a display control unit configured to arrange and display the three-dimensional radiation image of the right breast and the three-dimensional radiation image of the left breast, which have been aligned, and a tomographic image of the right region and a tomographic image of the left region, substantially symmetrically; and
(7) an operation unit configured to change a section position of one of the tomographic image of the right region and the tomographic image of the left region,
wherein the display control unit (a) changes a section position of the other tomographic image of the tomographic image of the right region and the tomographic image of the left region in conjunction with a change in the section position of the one tomographic image by the operation unit, in a case that the alignment unit has performed alignment between the three-dimensional radiation image of the right region and the three-dimensional radiation image of the left region, and (b) substantially symmetrically arranges and displays (i) the tomographic image of the right region that corresponds to the changed section position of the tomographic image of the right region and (ii) the tomographic image of the left region that corresponds to the changed section position of the tomographic image of the left region.

11. An image processing method comprising:
obtaining a three-dimensional radiation image of a right region of substantially symmetrical regions;
obtaining a three-dimensional radiation image of a left region of the substantially symmetrical regions;
performing alignment between the three-dimensional radiation image of the right region and the three-dimensional radiation image of the left region based on a feature position of the regions;
substantially symmetrically arranging and displaying the three-dimensional radiation image of the right region and the three-dimensional radiation image of the left region which have been aligned, and a tomographic image of the right region and a tomographic image of the left region; and
changing a section position of one of the tomographic image of the right region and the tomographic image of the left region,
wherein a section position of the other tomographic image of the tomographic image of the right region and the tomographic image of the left region is changed and displayed in conjunction with a change in the section position of the one tomographic image, in a case that alignment between the three-dimensional radiation image of the right region and the three-dimensional radiation image of the left region has been performed, and
wherein substantially symmetrically arranging and displaying are carried out for (i) the tomographic image of the right region that corresponds to the changed section position of the tomographic image of the right region and (ii) the tomographic image of the left region that corresponds to the changed section position of the tomographic image of the left region.

12. A non-transitory computer-readable storage medium storing a computer program for causing a computer to execute an image processing method, the method comprising:
obtaining a three-dimensional radiation image of a right region of substantially symmetrical regions;
obtaining a three-dimensional radiation image of a left region of the substantially symmetrical regions;
performing alignment between the three-dimensional radiation image of the right region and the three-dimensional radiation image of the left region based on a feature position of the regions;
substantially symmetrically arranging and displaying the three-dimensional radiation image of the right region and the three-dimensional radiation image of the left region which have been aligned, and a tomographic image of the right region and a tomographic image of the left region; and changing a section position of one of the tomographic image of the right region and the tomographic image of the left region, wherein a section position of the other tomographic image of the tomographic image of the right region and the tomographic image of the left region is changed and displayed in conjunction with a change in the section position of the one tomographic image, in a case that alignment between the three-dimensional radiation image of the right region and the three-dimensional radiation image of the left region has been performed, and wherein substantially symmetrically arranging and displaying are carried out for (i) the tomographic image of the right region that corresponds to the changed section position of the tomographic image of the right region and (ii) the tomographic image of the left region that corresponds to the changed section position of the tomographic image of the left region.

* * * * *